(12) United States Patent
McCullough

(10) Patent No.: US 11,497,249 B2
(45) Date of Patent: Nov. 15, 2022

(54) DRUG DELIVERY SYSTEM WITH STACKABLE SUBSTRATES

(71) Applicant: Vapor Cartridge Technology LLC, Stillwater, MN (US)

(72) Inventor: Timothy McCullough, Stillwater, MN (US)

(73) Assignee: Vapor Cartridge Technology LLC, Stillwater, MN (US)

(*) Notice: Subject to any disclaimer, the term of this patent is extended or adjusted under 35 U.S.C. 154(b) by 0 days.

(21) Appl. No.: 17/597,710

(22) PCT Filed: Jul. 9, 2020

(86) PCT No.: PCT/US2020/041446
§ 371 (c)(1),
(2) Date: Jan. 19, 2022

(87) PCT Pub. No.: WO2021/055079
PCT Pub. Date: Mar. 25, 2021

(65) Prior Publication Data
US 2022/0256921 A1    Aug. 18, 2022

Related U.S. Application Data

(60) Provisional application No. 63/023,998, filed on May 13, 2020, provisional application No. 62/901,073, filed on Sep. 16, 2019.

(51) Int. Cl.
*A24F 40/42* (2020.01)
*A61M 11/04* (2006.01)
(Continued)

(52) U.S. Cl.
CPC .............. *A24F 40/42* (2020.01); *A24F 40/20* (2020.01); *A24F 40/46* (2020.01); *A24F 40/70* (2020.01);
(Continued)

(58) Field of Classification Search
CPC ........ A61M 11/042; A61M 2205/0233; A61M 2205/0238; A24F 40/20; A24F 40/42; A24F 40/46; A24F 40/70
See application file for complete search history.

(56) References Cited

U.S. PATENT DOCUMENTS 3,270,437 A   9/1966 Castillo et al.
3,625,214 A   12/1971 Higuchi
(Continued)

FOREIGN PATENT DOCUMENTS

CN   109527660 A   3/2019
WO   WO-1994009842 A1   5/1994
(Continued)

OTHER PUBLICATIONS

US 9,254,008 B2, 02/2016, McCullough (withdrawn)
(Continued)

*Primary Examiner* — Valerie L Woodward
(74) *Attorney, Agent, or Firm* — Schwegman Lundberg & Woessner, P.A.

(57) ABSTRACT

The present invention is directed to an electrically conductive substrate (1002) coated with one or more herbal essences wherein the substrate may be a flat sheet of conductive metal or polymer. The coating (1120) may be present as separate sections on the substrate and multiple conductor contacts may be present on the substrate or may be separate components. Multiple coated substrates may be stacked together to form a cartridge for use in an herbal essence delivery device.

17 Claims, 27 Drawing Sheets

(51) Int. Cl.
*A24F 40/70* (2020.01)
*A24F 40/46* (2020.01)
*A24F 40/20* (2020.01)

(52) U.S. Cl.
CPC ... *A61M 11/042* (2014.02); *A61M 2205/0233* (2013.01); *A61M 2205/0238* (2013.01)

(56) References Cited

U.S. PATENT DOCUMENTS

| | | |
|---|---|---|
| 4,543,275 A | 9/1985 | Akashi et al. |
| 4,913,865 A | 4/1990 | Toyotama |
| 4,922,901 A | 5/1990 | Brooks |
| 5,060,671 A | 10/1991 | Counts et al. |
| 5,095,921 A | 3/1992 | Losee et al. |
| 5,224,498 A | 7/1993 | Deevi et al. |
| 5,269,327 A | 12/1993 | Counts et al. |
| 5,544,646 A | 8/1996 | Lloyd et al. |
| 5,878,752 A | 3/1999 | Adams et al. |
| 5,935,388 A | 8/1999 | Meszaros |
| 6,045,864 A | 4/2000 | Lyons et al. |
| 6,095,153 A | 8/2000 | Kessler et al. |
| 6,270,839 B1 | 8/2001 | Onoe et al. |
| 6,513,524 B1 | 2/2003 | Storz |
| 6,589,395 B1 | 7/2003 | Meili |
| 6,630,507 B1 | 10/2003 | Hampson et al. |
| 6,909,839 B2 | 6/2005 | Wang et al. |
| 7,025,992 B2 | 4/2006 | Whittle |
| 7,088,914 B2 | 8/2006 | Whittle et al. |
| 7,109,245 B2 | 9/2006 | Kunos et al. |
| 7,132,128 B2 | 11/2006 | Brcka |
| 7,215,878 B2 | 5/2007 | Neumann et al. |
| 7,279,421 B2 | 10/2007 | Suzuki |
| 7,344,736 B2 | 3/2008 | Whittle et al. |
| 7,399,872 B2 | 7/2008 | Webster et al. |
| 7,402,686 B2 | 7/2008 | Duchek |
| 7,524,881 B2 | 4/2009 | Goodwin et al. |
| 7,540,286 B2 | 6/2009 | Cross et al. |
| 7,622,140 B2 | 11/2009 | Whittle et al. |
| 7,651,570 B2 | 1/2010 | Brcka |
| 7,674,922 B2 | 3/2010 | Burdick et al. |
| 7,700,368 B2 | 4/2010 | Flockhart et al. |
| 7,709,536 B2 | 5/2010 | WHittle |
| 7,741,365 B2 | 6/2010 | Makriyannis et al. |
| 7,763,311 B2 | 7/2010 | Suzuki |
| 7,816,143 B2 | 10/2010 | Day |
| 7,913,688 B2 | 3/2011 | Cross et al. |
| 7,942,147 B2 | 5/2011 | Hodges et al. |
| 8,034,843 B2 | 10/2011 | Whittle et al. |
| 8,074,644 B2 | 12/2011 | Hale et al. |
| 8,147,898 B2 | 4/2012 | Coates |
| 8,161,979 B1 | 4/2012 | Sinclair, Jr. |
| 8,387,612 B2 | 3/2013 | Damani et al. |
| 8,481,091 B2 | 7/2013 | Ross |
| 8,512,767 B2 | 8/2013 | Ross |
| 8,910,630 B2 | 12/2014 | Todd |
| 8,910,640 B2 | 12/2014 | Sears et al. |
| 9,220,294 B2 | 12/2015 | McCullough |
| 9,333,229 B2 | 5/2016 | Bjorncrantz |
| 9,380,813 B2 | 7/2016 | McCullough |
| 9,408,986 B2* | 8/2016 | McCullough .......... B01D 11/00 |
| 9,775,379 B2 | 10/2017 | Davidson et al. |
| 9,802,011 B2 | 10/2017 | Davidson et al. |
| 9,839,241 B2 | 12/2017 | Davidson et al. |
| 9,993,602 B2 | 6/2018 | Davidson et al. |
| 10,034,990 B2 | 7/2018 | McCullough |
| D825,102 S | 8/2018 | Bowen et al. |
| 10,045,567 B2 | 8/2018 | Monsees et al. |
| 10,045,568 B2 | 8/2018 | Monsees et al. |
| 10,058,124 B2 | 8/2018 | Monsees et al. |
| 10,058,129 B2 | 8/2018 | Monsees et al. |
| 10,058,130 B2 | 8/2018 | Monsees et al. |
| 10,070,669 B2 | 9/2018 | Monsees et al. |
| 10,076,139 B2 | 9/2018 | Monsees et al. |
| 10,080,851 B2 | 9/2018 | Davidson et al. |
| 10,099,020 B2 | 10/2018 | Davidson et al. |
| 10,104,915 B2 | 10/2018 | Bowen et al. |
| 10,111,470 B2 | 10/2018 | Monsees et al. |
| 10,117,465 B2 | 11/2018 | Monsees et al. |
| 10,117,466 B2 | 11/2018 | Monsees et al. |
| 10,118,006 B2 | 11/2018 | Davidson et al. |
| 10,130,123 B2 | 11/2018 | Hatton et al. |
| 10,159,282 B2 | 12/2018 | Monsees et al. |
| 10,166,349 B2 | 1/2019 | Davidson et al. |
| D842,536 S | 3/2019 | Bowen et al. |
| 10,231,484 B2 | 3/2019 | Bowen et al. |
| 10,244,793 B2 | 4/2019 | Monsees et al. |
| 10,279,934 B2 | 5/2019 | Christensen et al. |
| D857,879 S | 8/2019 | Kurgan et al. |
| 10,369,304 B2 | 8/2019 | Davidson et al. |
| D858,745 S | 9/2019 | Kurgan et al. |
| D858,868 S | 9/2019 | Bowen et al. |
| D858,869 S | 9/2019 | Bowen et al. |
| D858,870 S | 9/2019 | Bowen et al. |
| D860,523 S | 9/2019 | Cheung et al. |
| 10,661,036 B2 | 5/2020 | McCullough |
| 10,821,240 B2 | 11/2020 | McCullough |
| 11,395,891 B2 | 7/2022 | McCullough |
| 2002/0117175 A1 | 8/2002 | Kottayil et al. |
| 2003/0015197 A1* | 1/2003 | Hale .................. A61K 31/519 128/200.14 |
| 2003/0131843 A1 | 7/2003 | Lu |
| 2003/0221625 A1 | 12/2003 | Toda et al. |
| 2004/0096402 A1 | 5/2004 | Hodges et al. |
| 2004/0126326 A1 | 7/2004 | Rabinowitz et al. |
| 2004/0138293 A1 | 7/2004 | Werner et al. |
| 2004/0147767 A1 | 7/2004 | Whittle et al. |
| 2005/0042172 A1 | 2/2005 | Whittle et al. |
| 2005/0063686 A1* | 3/2005 | Whittle ................ A61M 11/041 392/390 |
| 2006/0039959 A1 | 2/2006 | Wessling |
| 2006/0160888 A1 | 7/2006 | Kottayil et al. |
| 2006/0167084 A1 | 7/2006 | Dudley |
| 2007/0020193 A1 | 1/2007 | de Vries et al. |
| 2007/0041994 A1 | 2/2007 | McDowell |
| 2007/0049645 A1 | 3/2007 | Mechoulam et al. |
| 2007/0099987 A1 | 5/2007 | Weiss et al. |
| 2007/0113789 A1 | 5/2007 | Brcka |
| 2008/0057117 A1 | 3/2008 | Werner et al. |
| 2008/0110454 A1 | 5/2008 | White et al. |
| 2008/0112895 A1 | 5/2008 | Kottayil et al. |
| 2008/0181942 A1 | 7/2008 | Zajicek |
| 2008/0216828 A1 | 9/2008 | Wensley et al. |
| 2008/0255224 A1 | 10/2008 | Blum |
| 2008/0262099 A1 | 10/2008 | Whittle et al. |
| 2008/0275237 A1 | 11/2008 | Arslantas et al. |
| 2008/0306285 A1 | 12/2008 | Hale et al. |
| 2009/0005461 A1 | 1/2009 | Nagarkatti et al. |
| 2009/0197941 A1 | 8/2009 | Guy et al. |
| 2009/0324797 A1 | 12/2009 | Bobzin et al. |
| 2010/0012118 A1 | 1/2010 | Storz |
| 2010/0119606 A1 | 5/2010 | Whittle et al. |
| 2010/0158973 A1 | 6/2010 | Weiss et al. |
| 2010/0204312 A1 | 8/2010 | McAllister et al. |
| 2010/0204443 A1 | 8/2010 | Gazit et al. |
| 2010/0239635 A1 | 9/2010 | McClain et al. |
| 2010/0239693 A1 | 9/2010 | Guy et al. |
| 2010/0249223 A1 | 9/2010 | Di Marzo et al. |
| 2010/0304391 A1 | 12/2010 | Lombard |
| 2011/0036346 A1 | 2/2011 | Cohen et al. |
| 2011/0052694 A1 | 3/2011 | Stinchcomb et al. |
| 2011/0071178 A1 | 3/2011 | Makriyannis et al. |
| 2011/0073120 A1 | 3/2011 | Adamic |
| 2011/0082195 A1 | 4/2011 | Guy et al. |
| 2011/0097283 A1 | 4/2011 | Van Damme et al. |
| 2011/0240022 A1 | 10/2011 | Hodges et al. |
| 2012/0138050 A1 | 6/2012 | Wondka et al. |
| 2012/0304990 A1 | 12/2012 | Todd |
| 2012/0311744 A1 | 12/2012 | Sirkowski |
| 2013/0087144 A1 | 4/2013 | Todd |
| 2013/0152922 A1 | 6/2013 | Benassayag et al. |
| 2013/0178453 A1 | 7/2013 | Rohde et al. |
| 2013/0196960 A1 | 8/2013 | Rohde et al. |
| 2013/0255702 A1 | 10/2013 | Griffith, Jr. et al. |

(56) References Cited

U.S. PATENT DOCUMENTS

| | | | |
|---|---|---|---|
| 2013/0276799 A1* | 10/2013 | Davidson | A61M 15/0003 131/273 |
| 2013/0284192 A1 | 10/2013 | Peleg et al. | |
| 2013/0298905 A1 | 11/2013 | Levin et al. | |
| 2014/0041655 A1 | 2/2014 | Barron et al. | |
| 2014/0060554 A1 | 3/2014 | Collett et al. | |
| 2015/0075546 A1 | 3/2015 | Kueny, Sr. et al. | |
| 2015/0136158 A1 | 5/2015 | Stevens et al. | |
| 2015/0223515 A1 | 8/2015 | Mccullough | |
| 2015/0223523 A1* | 8/2015 | McCullough | A61K 36/28 131/328 |
| 2016/0082203 A1 | 3/2016 | Mccullough et al. | |
| 2016/0286860 A1 | 10/2016 | Flayler | |
| 2016/0310682 A1 | 10/2016 | Mccullough | |
| 2016/0310684 A1 | 10/2016 | Mccullough | |
| 2016/0331035 A1 | 11/2016 | Cameron | |
| 2016/0331036 A1 | 11/2016 | Cameron | |
| 2016/0354561 A1 | 12/2016 | Mccullough | |
| 2017/0360089 A1 | 12/2017 | Davidson et al. | |
| 2018/0318529 A1 | 11/2018 | Davidson et al. | |
| 2018/0344954 A1 | 12/2018 | Davidson et al. | |
| 2019/0009039 A1 | 1/2019 | Davidson et al. | |
| 2019/0290862 A1 | 9/2019 | Davidson et al. | |
| 2020/0222644 A1 | 7/2020 | Mccullough | |

FOREIGN PATENT DOCUMENTS

| | | |
|---|---|---|
| WO | WO-2001076768 A1 | 10/2001 |
| WO | WO-2008134668 A2 | 11/2008 |
| WO | WO-2010011464 A1 | 1/2010 |
| WO | WO-2010111232 A9 | 3/2011 |
| WO | WO-2011100359 A1 | 8/2011 |
| WO | WO-2012085919 A2 | 6/2012 |
| WO | WO-2013083631 A1 | 6/2013 |
| WO | WO-2013164761 A1 | 11/2013 |
| WO | WO-2015123064 A1 | 8/2015 |
| WO | WO-2015123317 A1 | 8/2015 |
| WO | WO-2021055079 A1 | 3/2021 |

OTHER PUBLICATIONS

U.S. Appl. No. 14/264,999 U.S. Pat. No. 9,220,294, filed Apr. 29, 2014, Methods and Devices Using Cannabis Vapors.

U.S. Appl. No. 14/959,591 U.S. Pat. No. 9,408,986, filed Dec. 4, 2015, Methods and Devices Using Cannabis Vapors.

U.S. Appl. No. 14/574,591 U.S. Pat. No. 9,380,813, filed Dec. 18, 2014, Drug Delivery System and Method.

U.S. Appl. No. 15/201,185 U.S. Pat. No. 10,034,990, filed Jul. 1, 2016, Drug Delivery System and Method.

U.S. Appl. No. 15/118,090 U.S. Pat. No. 10,821,240, filed Aug. 10, 2016, Methods and Drug Delivery Devices Using Cannabis.

U.S. Appl. No. 15/199,366 U.S. Pat. No. 10,661,036, filed Jun. 30, 2016, Methods and Delivery Devices Using Herbal Extracts.

U.S. Appl. No. 16/823,200, filed Mar. 18, 2020, Methods and Delivery Devices Using Herbal Extracts.

"Crafty Operating Manual", Storz & Bickel GMBH & Co. KG, (2015), 1-34.

"Volcano Operating Manual", Storz & Bickel GMBH & Co. KG, (2015), 36 pgs.

"7 Things You Need To Know About Sativex", LeafScience, http://www.leafscience.com/2014/03/08/7-things-need-know-sativex/, (Mar. 8, 2014), 13 pgs.

"710 Pen ARK", About 710pen, [Online]. [Accessed Nov. 28, 2017]. Retrieved from the Internet: <URL: https://www.710penvape.com/pages/about-us-1>, 1 pg.

"Alexza Pharmaceuticals: Staccato Platform Details", [Online]. Retrieved from the Internet: <URL: http://www.alexza.com/staccato/staccato-platform>, (Accessed on: Jun. 30, 2015), 5 pgs.

"Amazon.com: EZ Breathe Atomizer Asthma-Inhalers, Model # EZ100: Health & Personal Care", [Online]. Retrieved from the Internet: <URL: http://www.amazon.com/EZ-Breathe-Atomizer-Asthma-Inhalers-EZ-100/dp/B00DQSTVRQ/ref=pd_sxp_f_pt>, (Accessed: Mar. 3, 2015), 25 pgs.

"U.S. Appl. No. 14/264,999, Non Final Office Action dated Mar. 13, 2015", 10 pgs.

"U.S. Appl. No. 14/264,999, Notice of Allowance dated Jul. 2, 2015", 8 pgs.

"U.S. Appl. No. 14/264,999, Notice of Allowance dated Nov. 9, 2015", 8 pgs.

"U.S. Appl. No. 14/264,999, Response filed Jun. 12, 2015 to Non Final Office Action dated Mar. 13, 2015", 16 pgs.

"U.S. Appl. No. 14/574,591, Non Final Office Action dated Aug. 18, 2015", 14 pgs.

"U.S. Appl. No. 14/574,591, Notice of Allowance dated Feb. 12, 2016", 5 pgs.

"U.S. Appl. No. 14/574,591, Notice of Allowance dated May 20, 2016", 5 pgs.

"U.S. Appl. No. 14/574,591, Notice of Allowance dated Nov. 24, 2015", 5 pgs.

"U.S. Appl. No. 14/574,591, Response filed Jun. 30, 2015 to Restriction Requirement dated May 21, 2015", 9 pgs.

"U.S. Appl. No. 14/574,591, Restriction Requirement dated May 21, 2015", 5 pgs.

"U.S. Appl. No. 14/574,591, Response filed Oct. 30, 2015 to Non Final Office Action dated Aug. 18, 2015", 44 pgs.

"U.S. Appl. No. 14/959,591, Non Final Office Action dated Feb. 1, 2016", 12 pgs.

"U.S. Appl. No. 14/959,591, Notice of Allowance dated Jun. 8, 2016", 8 pgs.

"U.S. Appl. No. 14/959,591, Preliminary Amendment filed Dec. 10, 2015", 6 pgs.

"U.S. Appl. No. 14/959,591, Response filed Apr. 29, 2016 to Non Final Office Action dated Feb. 1, 2016", 24 pgs.

"U.S. Appl. No. 15/118,090, Final Office Action dated Aug. 8, 2019", 7 pgs.

"U.S. Appl. No. 15/118,090, Non Final Office Action dated Feb. 24, 2020", 7 pgs.

"U.S. Appl. No. 15/118,090, Non Final Office Action dated Dec. 14, 2018", 21 pgs.

"U.S. Appl. No. 15/118,090, Notice of Allowance dated Jun. 25, 2020", 9 pgs.

"U.S. Appl. No. 15/118,090, Response filed Feb. 6, 2020 to Final Office Action dated Aug. 8, 2019", 10 pgs.

"U.S. Appl. No. 15/118,090, Response filed May 26, 2020 to Non Final Office Action dated Feb. 24, 2020", 2 pgs.

"U.S. Appl. No. 15/118,090, Response filed Jun. 14, 2019 to Non Final Office Action dated Dec. 14, 2019", 21 pgs.

"U.S. Appl. No. 15/188,190, Supplemental Preliminary Amendment filed Nov. 27, 2017", 7 pgs.

"U.S. Appl. No. 15/199,366 Response filed Nov. 22, 2017 to Non Final Office Action dated Aug. 25, 2017.", 10 pgs.

"U.S. Appl. No. 15/199,366, Corrected Notice of Allowability dated Mar. 18, 2020", 2 pgs.

"U.S. Appl. No. 15/199,366, Final Office Action dated Nov. 21, 2019", 11 pgs.

"U.S. Appl. No. 15/199,366, Non Final Office Action dated Aug. 25, 2017", 13 pgs.

"U.S. Appl. No. 15/199,366, Notice of Allowance dated Feb. 5, 2020", 5 pgs.

"U.S. Appl. No. 15/199,366, Response filed Jan. 21, 2020 to Final Office Action dated Nov. 21, 2019", 7 pgs.

"U.S. Appl. No. 15/201,185, Corrected Notice of Allowability dated Jun. 29, 2018", 3 pgs.

"U.S. Appl. No. 15/201,185, Non Final Office Action dated Aug. 25, 2017", 8 pgs.

"U.S. Appl. No. 15/201,185, Notice of Allowance dated Mar. 28, 2018", 5 pgs.

"U.S. Appl. No. 15/201,185, Notice of Allowance dated Jun. 29, 2018", 3 pgs.

"U.S. Appl. No. 15/201,185, Response filed Nov. 27, 2017 to Non Final Office Action dated Aug. 25, 2017", 7 pgs.

"U.S. Appl. No. 16/823,200, Corrected Notice of Allowability dated Mar. 25, 2022", 8 pgs.

(56) References Cited

OTHER PUBLICATIONS

"U.S. Appl. No. 16/823,200, Non Final Office Action dated Jan. 21, 2022", 8 pgs.
"U.S. Appl. No. 16/823,200, Notice of Allowance dated Mar. 9, 2022", 7 pgs.
"U.S. Appl. No. 16/823,200, Preliminary Amendment filed Jul. 27, 2020", 6 pgs.
"U.S. Appl. No. 16/823,200, Response filed Jan. 24, 2022 to Non Final Office Action dated Jan. 21, 2022", 8 pgs.
"Big Pharma's Weed Winner", [online]. The Daily Beast. [retrieved on Apr. 29, 2014]., Retrieved from the Internet: <URL: http://www.thedailybeast.com/articles/2014/01/24/how-one-pharmaceutical-company-could-become-the-safest-and-most-trusted-of-all-cannabis-dealers.html#url=/articles/2014/01/24/how-one-pharmaceutical-company-could-become-, (Jan. 24, 2014), 19 pgs.
"Canadian Application Serial No. 2,934,983, Office Action dated Apr. 12, 2018", 3 pgs.
"Canadian Application Serial No. 2,934,983, Office Action dated Aug. 31, 2017", 3 pgs.
"Canadian Application Serial No. 2,934,983, Response filed Feb. 8, 2018 to Office Action dated Aug. 31, 2017", 35 pgs.
"Canadian Application Serial No. 2,934,983, Response filed Oct. 9, 2018 to Office Action dated Apr. 12, 2018", 16 pgs.
"Canadian Application Serial No. 2,939,088, Office Action dated Jan. 8, 2019", 3 pgs.
"Canadian Application Serial No. 2,939,088, Office Action dated Apr. 16, 2018", 3 pgs.
"Canadian Application Serial No. 2,939,088, Office Action dated Jul. 31, 2017", 3 pgs.
"Canadian Application Serial No. 2,939,088, Response filed Jan. 25, 2018 to Office Action dated Jul. 31, 2017", 126 pgs.
"Canadian Application Serial No. 2,939,088, Response filed Jul. 5, 2019 to Office Action dated Jan. 8, 2019", 11 pgs.
"Canadian Application Serial No. 2,939,088, Response filed Oct. 16, 2018 to Office Action dated Apr. 16, 2018", 17 pgs.
"Canadian Application Serial No. 3,075,070, Office Action dated Apr. 29, 2021", 4 pgs.
"Canadian Application Serial No. 3,075,070, Office Action dated Oct. 22, 2021", 3 pgs.
"Canadian Application Serial No. 3,075,070, Response filed Feb. 14, 2022 to Office Action dated Oct. 22, 2021", 16 pgs.
"Canadian Application Serial No. 3,075,070, Response filed Aug. 3, 2021 to Office Action dated Apr. 29, 2021", 13 pgs.
"Clean Your Volcano! How Often?", Volcano Vaporizer Tips n' Tricks, [Online]. Retrieved from the Internet: <URL: http://volcanotips.com/volcano/clean-your-volcano-how-often/, (Accessed Feb. 19, 2016), 4 pgs.
"Compare vaporizers", Storz & Bickel, [Online]. [Accessed Nov. 28, 2017]. Retrieved from the Internet: <URL: https://www.storz-bickel.com/us/en/compare/, 4 pgs.
"Crafty", SKU 01 00 CY—Storz & Bickel, [Online]. [Accessed Nov. 28, 2017]. Retrieved from the Internet: <URL: https://www.storz-bickel.com/us/en/crafty.html>, 5 pgs.
"Crafty Vaporizer", Storz & Bickel, [Online]. [Accessed Nov. 28, 2017]. Retrieved from the Internet: <URL: https://www.storz-bickel.com/us/en/crafty/>, 4 pgs.
"Decarboxylating Cannabis: Turning THCA into THC", [online}. [retrieved on Apr. 29, 2014]. Retrieved from the Internet: <URL: http://www.marijuanagrowershq.com/decarboxylating-cannabis-turning-thca-into-thc/>, (Aug. 14, 2012), 36 pgs.
"Decarboxylation of cannabis: scientific info about temps and times", [online]. [archived on Jul. 5, 2013]. Retrieved from the Internet: <URL: http://cannabischris.com/2012/10/decarboxylation-of-cannabis/>, (Oct. 31, 2012), 5 pgs.
"Dr. Sisley Receives Government Grant to Research Cannabis and PTSD", [Online]. Retrieved from the Internet: <URL: https://www.cannabisreports.com/news/2014/12/17/dr-sisley-receives-government-grant-to-research-cannabis-and-ptsd/>, (Dec. 17, 2014), 10 pgs.

"Edibles in Review: LickIt Cannabis-Infused Breath Strips—Drugs Forum", [Online]. Retrieved from the Internet: <URL: https://drugs-forum.com/forum/showthread.php?t=220406>, (Accessed Apr. 26, 2016), 3 pgs.
"Evaluation Of Volcano(r) Vaporizer For The Efficient Emission Of THC, CBD, CBN And The Significant Reduction And/Or Elimination of Polynuclear-Aromatic (PNA) Analytes Resultant Of Pyrolysis", prepared by Chemic Laboratories, Canton, MA, [online}. [retrieved on Apr. 29, 2014]. Retrieved from the Internet: <URL: http://www.maps.org/mmj/vaporizerstudy4.15.03.pdf>, (2003), 57 pgs.
"Hash Oil", [online]. [retrieved on Apr. 29, 2014]. Retrieved from the Internet: <URL: http://en.wikipedia.org/wiki/Hash_oil>, (last modified on Apr. 27, 2014), 4 pgs.
"Haze Vaporizer", Guest Post—Best Marijuana Vaporizers For Your Health, [Online]. [Accessed Nov. 28, 2017]. Retrieved from the Internet: <URL: https://www.marijuana.com/news/2014/12/best-marijuana-vaporizers-for-your-health/>, (Dec. 11, 2014), 11 pgs.
"Heliospectra AB hires Dr. Sue Sisley as Director of Medicinal Plant Research", Heliospectra, [Online]. Retrieved from the Internet: <URL: https://www.heliospectra.com/blog/heliospectra-ab-hires-dr-sue-sisley-director-medicinal-plant-research>, (Feb. 23, 2015), 6 pgs.
"Herbal Vaporizer, Ingesting herbs has some incredible health benefits", Natural Health Ezine, [Online]. Retrieved from the Internet: <URL: http://naturalhealthezine.com/herbal-vaporizers-an-introduction/>, (Jan. 9, 2011), 5 pgs.
"History: GW Pharmaceuticals", [Online]. Retrieved from the Internet: <URL: http://www.gwpharm.com/history.aspx>, (Accessed on: Jun. 30, 2015), 5 pgs.
"How to Use Your Inhaler", Asthma Society of Canada, [Online]. Retrieved from the Internet: <URL: http://www.asthma.ca/adults/treatment/spacers.php, (Oct. 2015), 3 pgs.
"International Application Serial No. PCT/US2015/014418, International Preliminary Report on Patentability dated Aug. 25, 2016", 10 pgs.
"International Application Serial No. PCT/US2015/014418, International Search Report dated Jun. 25, 2015", 4 pgs.
"International Application Serial No. PCT/US2015/014418, Invitation to Pay Additional Fees and Partial Search Report dated Apr. 20, 2015", 2 pgs.
"International Application Serial No. PCT/US2015/014418, Written Opinion dated Jun. 25, 2015", 8 pgs.
"International Application Serial No. PCT/US2015/015445, International Preliminary Report on Patentability dated Aug. 25, 2016", 18 pgs.
"International Application Serial No. PCT/US2015/015445, International Search Report dated May 14, 2015", 4 pgs.
"International Application Serial No. PCT/US2015/015445, Written Opinion dated May 14, 2015", 16 pgs.
"International Application Serial No. PCT/US2020/041446, International Preliminary Report on Patentability dated Mar. 31, 2022", 10 pgs.
"International Application Serial No. PCT/US2020/041446, International Search Report dated Jan. 21, 2021", 7 pgs.
"International Application Serial No. PCT/US2020/041446, Invitation to Pay Additional Fees mailed Nov. 10, 2020", 10 pgs.
"International Application Serial No. PCT/US2020/041446, Written Opinion dated Jan. 21, 2021", 8 pgs.
"Juju Joints: Home page", [Online]. Retrieved from the Internet: <URL: http://jujujoints.com/>, (Accessed on: Jun. 30, 2015), 1 pg.
"Juju Joints: The Deets", [Online]. Retrieved from the Internet: <URL: http://jujujoints.com/deets/>, (Accessed on: Jun. 30, 2015), 3 pgs.
"Open Vape-Products: O.PENVAPE Battery & Charger", [Online]. Retrieved from the Internet: <URL: http://www.openvape.com/shop/shop/featured-products/o-penvape-battery.html?SID=h9susctdi7uc88huscks6je2o0>, (Accessed on: Jun. 30, 2015), 3 pgs.
"Open vape: Home page", [Online]. Retrieved from the Internet: <URL: http://www.openvape.com/>, (Accessed on: Jun. 30, 2015), 2 pgs.

(56) References Cited

OTHER PUBLICATIONS

"Sativex(r)",[online]. (c) 2014 GW Pharmaceuticals. [retrieved on Apr. 29, 2014]. Retrieved from the Internet: <URL: http://www.gwpharm.com/Sativex.aspx>, (2014), 2 pgs.
"Science Minus Details: 'Weed Science or Activation Explained!!'", [Online]. Retrieved from the Internet: <URL: http://www.scienceminusdetails.com/2009/04/weed-science.html, (2009), 17 pgs.
"The ARK by 710 Pen—Three pens, nine cartridges, ONE ARK!", Copyright 710 Pen, 2011-2014, [Online]. [Accessed Nov. 28, 2017]. Retrieved from the Internet: <URL: https://www.710penvape.com/products/the-new-710-ark-everything-you-need-in-1-kit>, 2 pgs.
"The World's First Programmable Drug Delivery System", Syqe Medical, [Online] Retrieved from the Internet: <URL: https://www.syqemedical.com/>, (Retrieved on Feb. 6, 2020), 16 pgs.
"Total Sublimation—Sublimator in Action", [online]. [retrieved on Apr. 29, 2014]. Retrieved from the Internet: <URL: http://thehighcanadian.wordpress.com/tag/total-sublimation/>, (2014), 3 pgs.
"Tutorial: Atomizer vs. Cartomizer vs. Clearomizer Overview of Atomizer vs. Cartomizer vs. Clearomizer", [Online]. Retrieved from the Internet: <URL: https://www.misthub.com/blog/tutorialatomizervscartomizervsclearomizer/>, (Accessed: Mar. 3, 2015), 15 pgs.
"Vacuum and fractional distillation", [online]. [retrieved on Apr. 29, 2014]. Retrieved from the Internet: <URL: http://boards.cannabis.com/concentrates/182951-vacuum-fractional-distillation.html>, (2014), 5 pgs.
"Vaporizer (inhalation device)", [online]. Wikipedia(r), the free encyclopedia. [retrieved on Apr. 29, 2014]. Retrieved from the Internet: <URL: http://en.wikipedia.org/wiki/Vaporizer_(inhalation_device)>, (modified on Mar. 21, 2014), 4 pgs.
"Volcano Vaporizer", [online]. Copyright 2013 Storz and Bickel GMBH and Co. KG. [retrieved on Dec. 10, 2013]. Retrieved from the Internet: <URL: http://volcanovaporizer.com/about/>, (2013), 4 pgs.
"Volcano(r) Vaporization System", [online]. [retrieved on May 15, 2014]. Retrieved from the Internet: <URL: http://www.storz-bickel.com/vaporizer/volcano-technology.html>, (2014), 4 pgs.
"Why Vaporize?", Copyright 2013 Storz and Bickel GMBH and Co. KG. [retrieved on Dec. 10, 2013]. Retrieved from the Internet: <URL: http://volcanovaporizer.com/whv-vape/>, (2013), 4 pgs.
Chambers, Rachel, "Leafly: What is Dabbing and How Do Dabs Work?", [Online]. Retrieved from the Internet: <URL: https://www.leafly.com/news/cannabis-101/is-dabbing-good-or-bad-or-both>, (Oct. 28, 2013), 9 pgs.
Cross, Green, "THC is heat activated: Rollitup", [Online]. Retrieved from the Internet: <URL: http://www.rollitup.org/t/thc-is-heat-activated.242205/>, (Accessed Apr. 26, 2016), 7 pgs.
Doblin, Rick, "HHS Cover Letter", Multidisciplinary Association for Psychedelic Studies(MAPS), [Online]. Retrieved from the Internet: <URL: http://www.maps.org/research-archive/mmj/HHS-CoverLetter-Doblin-electronic-14Mar14.pdf>, (Mar. 12, 2014), 2 pgs.
Fraleigh, Nicholas, "Backdoor Medicine: How Cannabis Suppositories Can Save Lives—Cannabis Digest", [Online]. Retrieved from the Internet: <URL: http://cannabisdigest.ca/cannatory/>, (2014), 53 pgs.
Greenberg, Tzally, "Eight Years and 83 Million Later, Syqe Medical Releases First Cannabis Inhaler", CTECH by Calcalist, [Online] Retrieved from the Internet: <URL: https://www.calcalistech.com/ctech/articles/0,7340,L-3764680,00.html>, (Jun. 20, 2019), 5 pgs.
Hazekamp, et al., "Evaluation of a Vaporizing Device (Volcano (R)) for the Pulmonary administration of tetrahydrocannabinol", Journal of Pharmaceutical Sciences. vol. 95, (Jun. 2006), 1308-1317.
Hazekamp, Arno, "", Cannabis Extracting The Medicine Hazekamp Thesis, (2007), 187 pgs.
Jimbob, "THC coated rolling papers: Cannabis.com—The World's Cannabis Site", [Online]. Retrieved from the Internet: <URL: http://boards.cannabis.com/threads/thc-coated-rolling-papers.114509/>, (Accessed Apr. 26, 2016), 7 pgs.
June-Wells, Mark, "Your Guide to Supercritical Extraction", Cannabis Business Times, [Online] Retrieved from the Internet on Oct. 1, 2019: <URL: https://www.cannabisbusinesstimes.com/article/your-guide-to-supercritical-extraction/>, (Mar. 2018), 7 pgs.
Mechoulam, Raphael, "Veterans for medical cannabis access: General use of cannabis for PTSD Symptoms", [Online]. Retrieved from the Internet: <URL: http://veteransformedicalmarijuana.org/content/general-use-cannabis-ptsd-symptoms>, (2010), 3 pgs.
Schwartz, Carly, "Marijuana Market Poised To Grow Faster Than Smartphones", [online]. Huffington Post. [retrieved on Apr. 29, 2014]. Retrieved from the Internet: <URL: http://www.huffingtonpost.com/2013/11/04/marijuana-market_n_4209874.html>, (2013), 6 pgs.
Wattenberg, Sarah, "Letter to Multidisciplinary Association for Psychedelic Studies (MAPS)", [Online]. Retrieved from the Internet: <URL: http://www.maps.org/research-archive/mmj/CoverletterSarahW_10-23_2013_final_forweb.pdf, (Oct. 23, 2013), 14 pgs.
Welch, William M., "Vaporizers, e-cigs of the pot world, are booming", [online]. USA Today. [retrieved on Apr. 29, 2014]. Retrieved from the Internet: <URL: http://www.usatoday.com/story/money/business/2014/03/15/marijuana-vapporizing-gains/6042675/>, (Mar. 17, 2014), 6 pgs.
Whittle, G. W, et al., "Prospect for new cannabis-based prescription medicines", Journal of Cannabis Therapeutics 3(4), (2001), 133-152.
"Canadian Application Serial No. 3,075,070, Office Action dated Apr. 13, 2022", 3 pgs.
"Mexican Application Serial No. MX/a/2022/003189, Response Filed May 24, 2022 to Office Action dated Apr. 20, 2022", W/ English Claims, 12 pgs.

\* cited by examiner

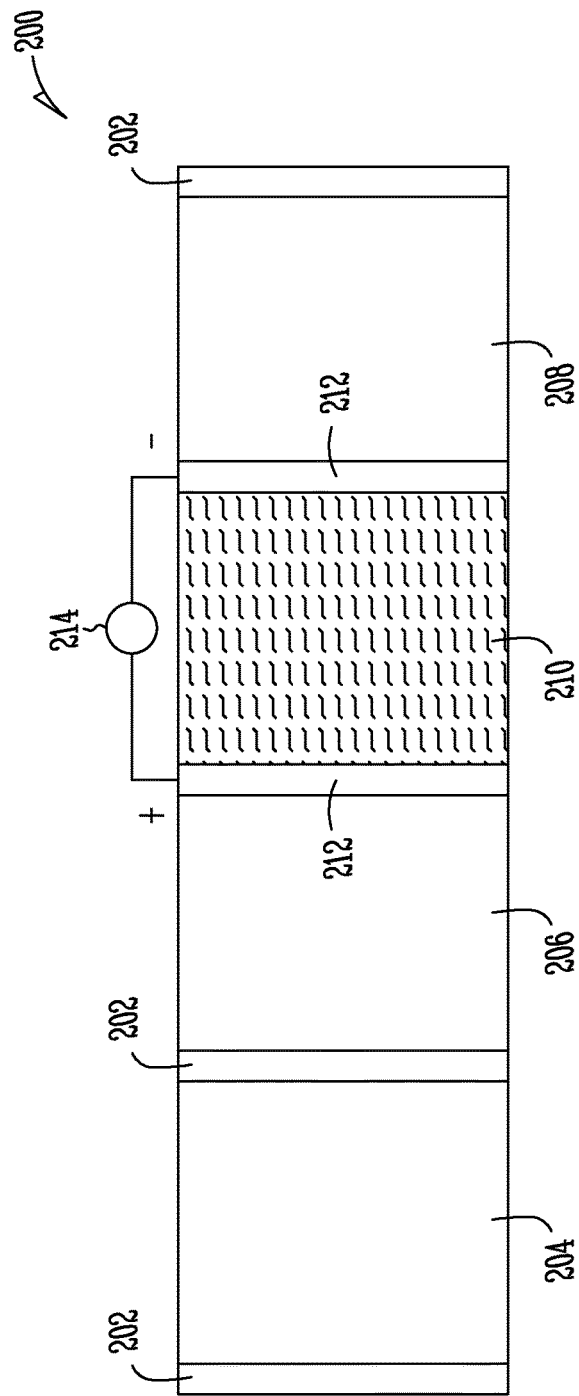
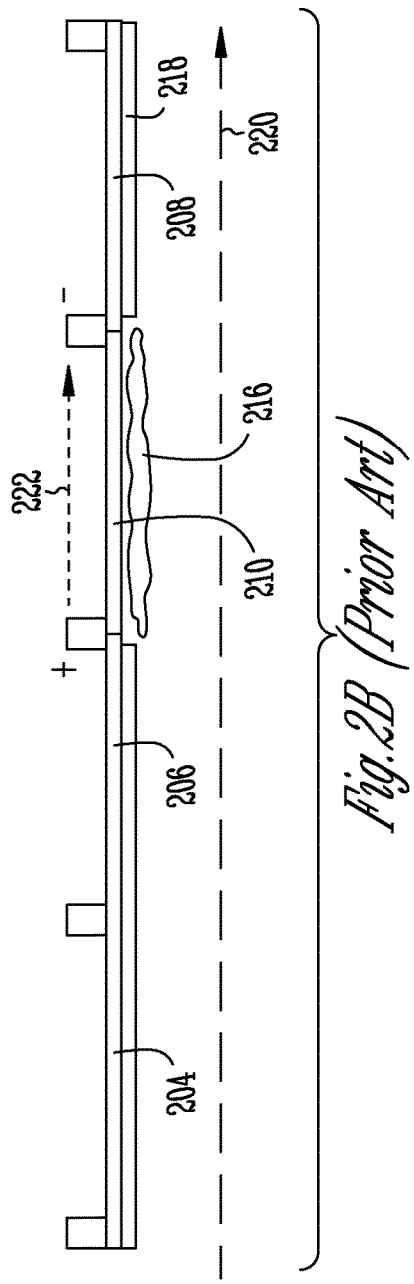
Fig. 2A (Prior Art)
Fig. 2B (Prior Art)

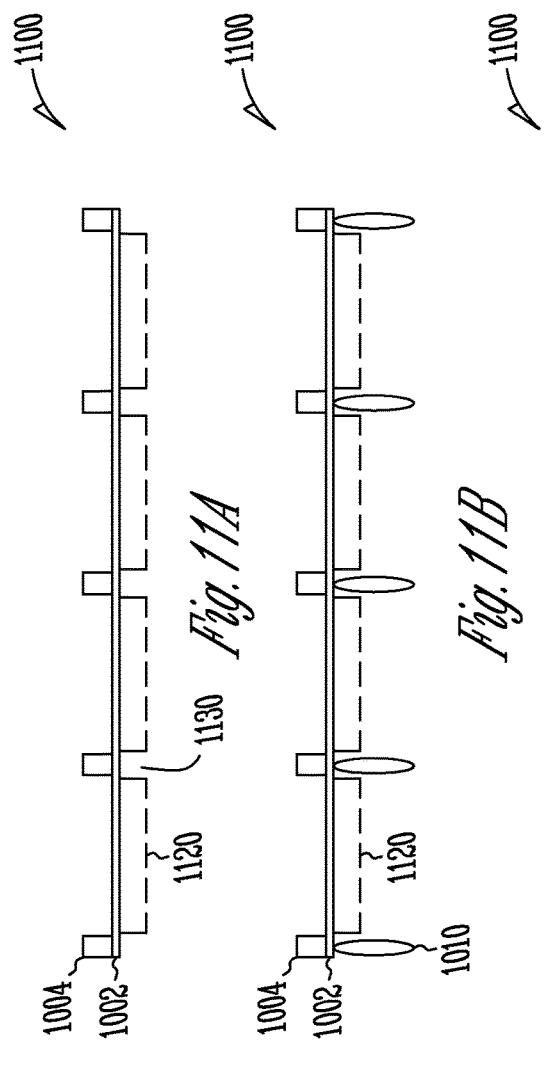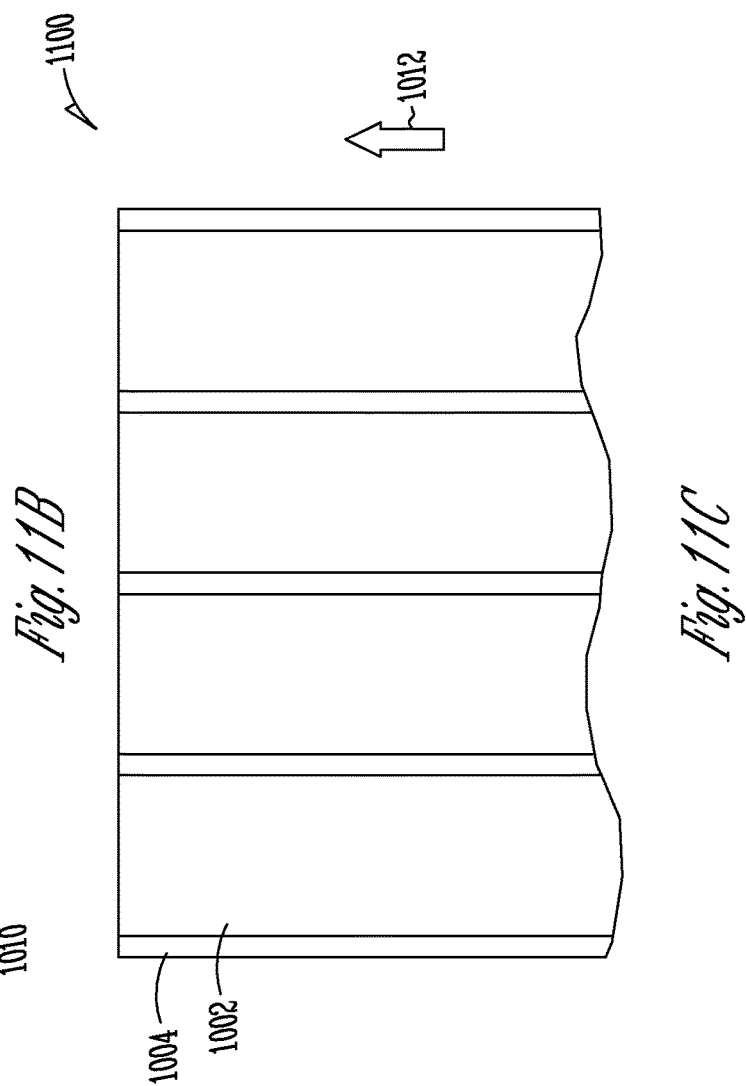

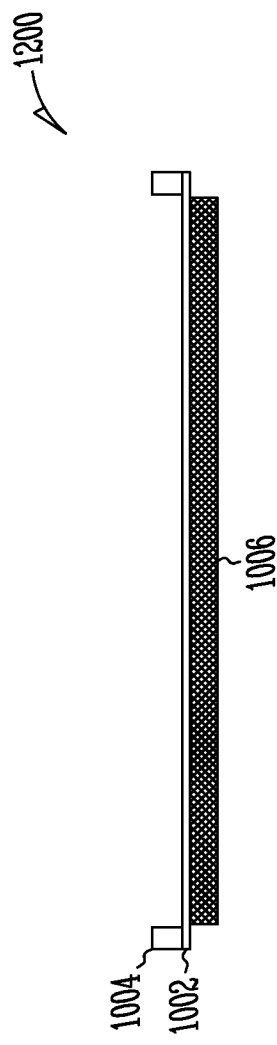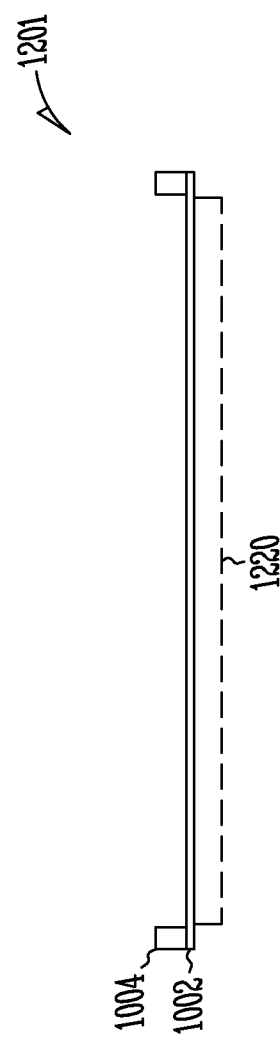

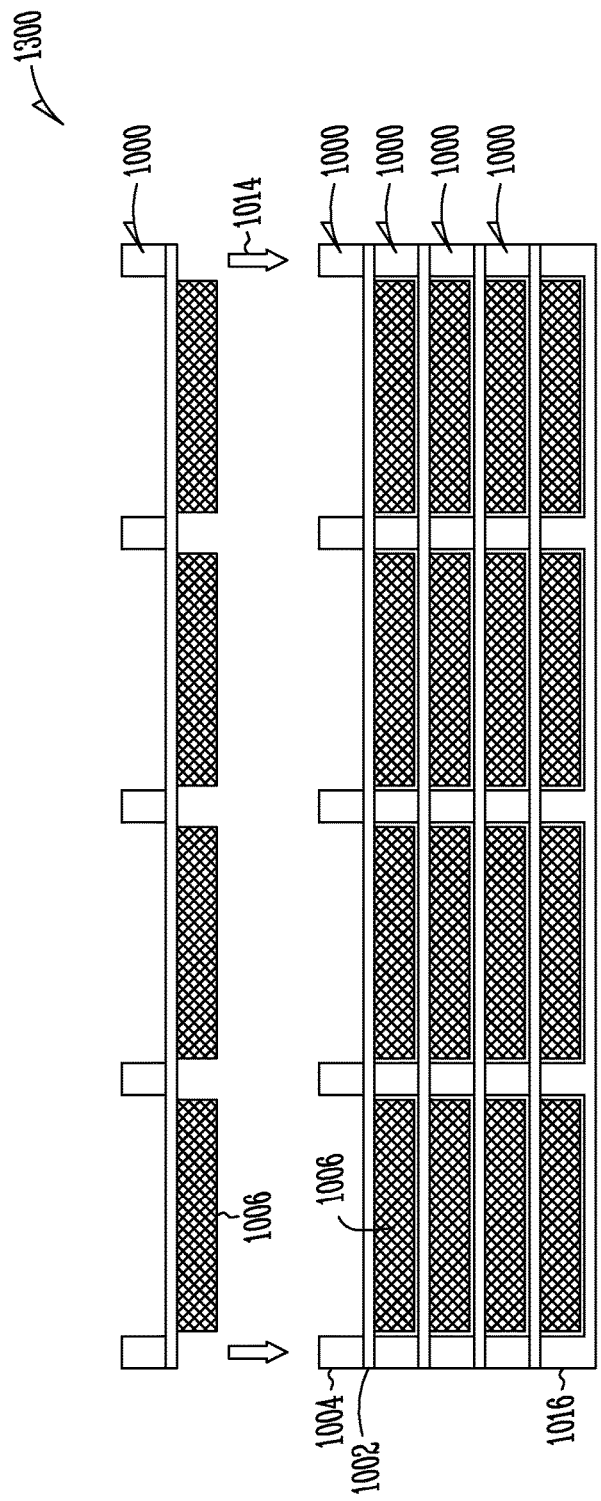
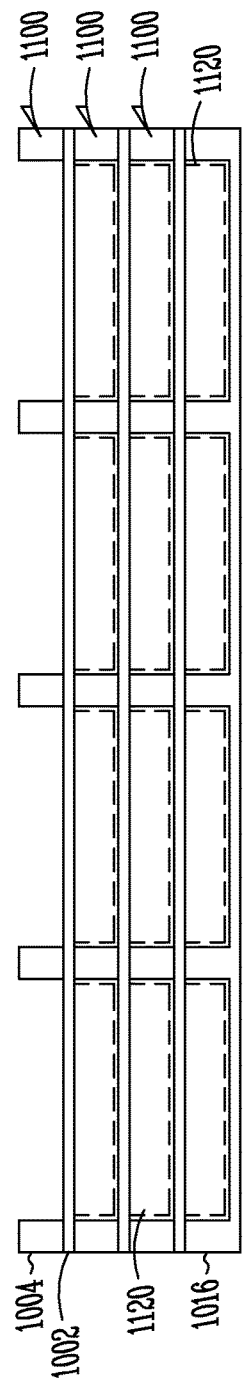

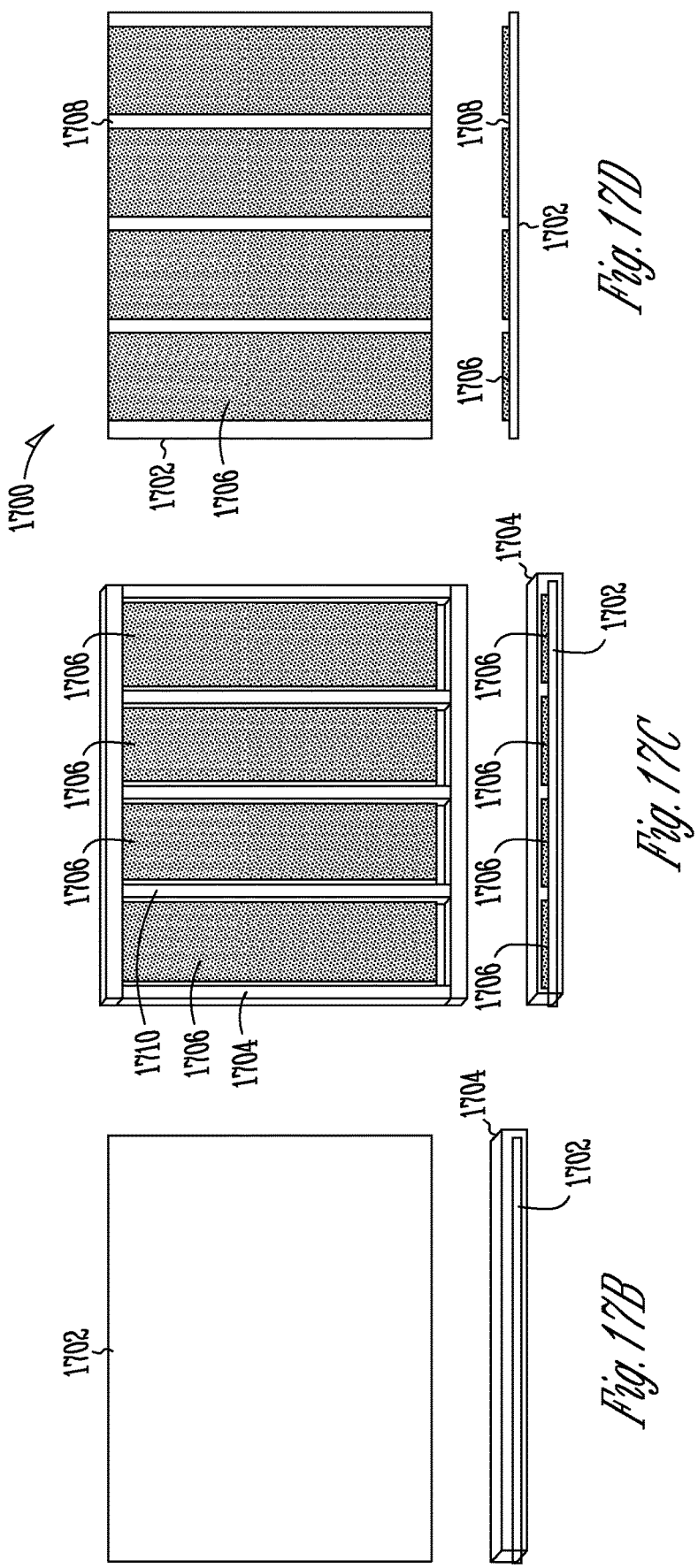

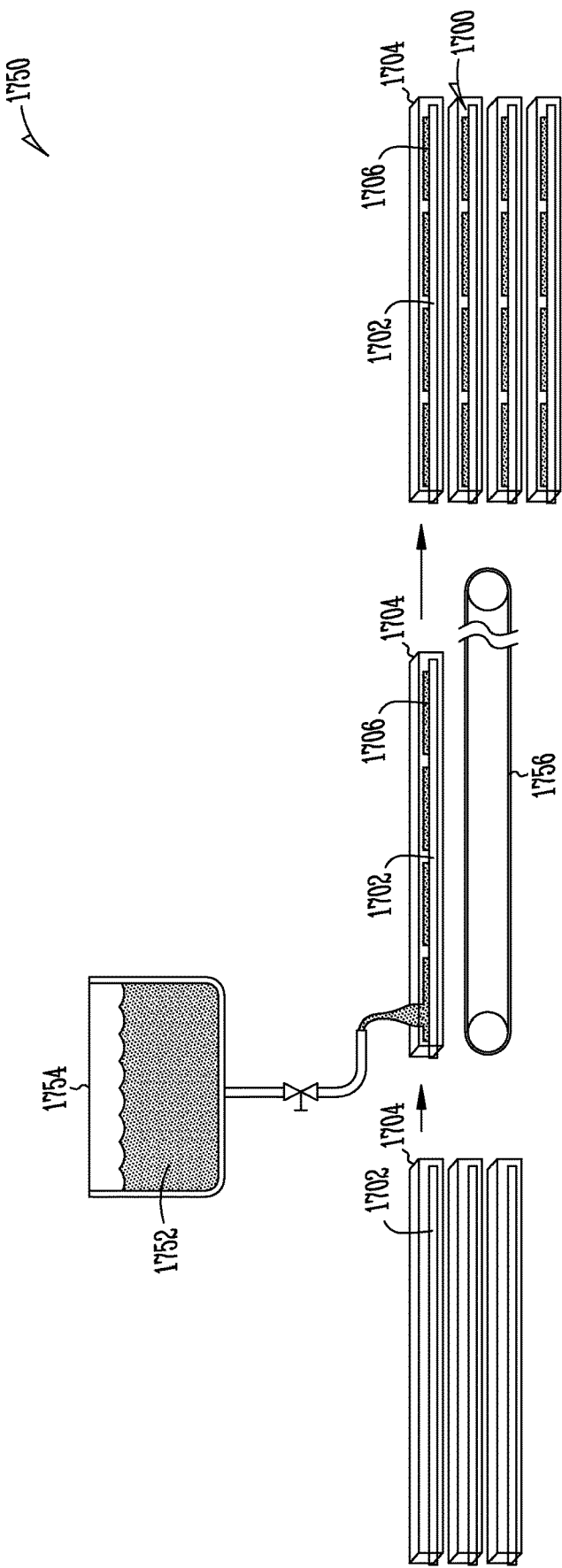

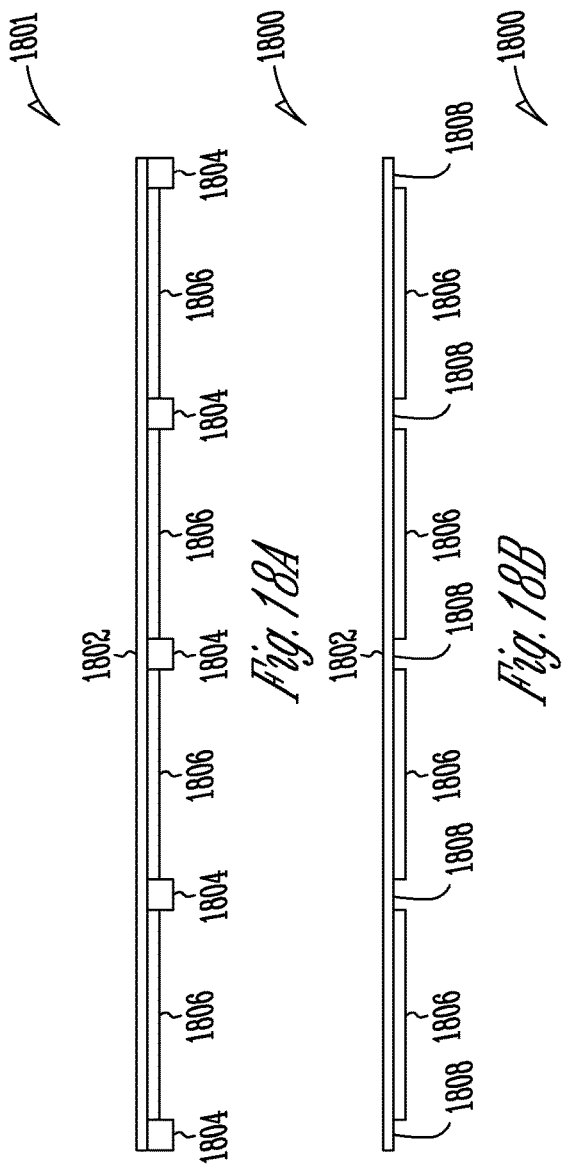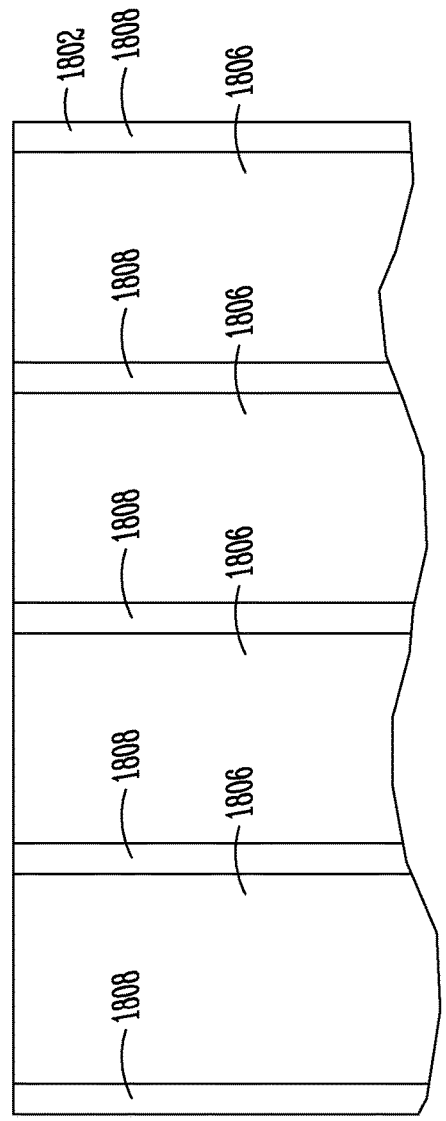

DRUG DELIVERY SYSTEM WITH STACKABLE SUBSTRATES

CLAIM OF PRIORITY

This patent application is a U.S. National Stage Filing under 35 U.S.C. from International Application No. PCT/US2020/041446, filed on Jul. 9, 2020, and published as WO 2021/055079 on Mar. 25, 2021, which application claims the benefit of priority to U.S. Provisional Application Ser. No. 63/023,998, filed May 13, 2020, and also claims the benefit of U.S. Provisional Application Ser. No. 62/901,073, filed. Sep. 16, 2019, which applications are both incorporated by reference herein in their entireties.

BACKGROUND

The Thermal Distillation and Wet Extraction Processes described in earlier applications and patents, including for example, U.S. Pat. Nos. 9,220,294 and 10,661,036 provide processes for preparation of herbal essence cartridges for use in vapor inhalation delivery systems. These processes enable regulated condensation or deposit of the herbal essence onto a conductive substrate which can be electronically managed to provide controlled re-volatilization of the herbal essence. This process is pictorially represented by FIG. 1. FIG. 1 shows a single sheet, single side coating process using heat to selective volatiles only the herbal essences such as cannabinoids that then condenses them onto a chilled substrate. These processes enable controlled, precisely metered delivery to the user or patient of appropriate dosages of herbal essences such as but not limited to cannabinoids, beneficial remedies such as menthol, camphor, echinacea extract as well as other herbal treatments.

The method for converting the coated substrate into a Vapor Cartridge is described in earlier applications and patents by Applicant, including for example, U.S. Pat. No. 9,408,986. The Vapor Cartridge can be constructed from an extruded aluminum substrate. Liquid aluminum can be extruded to create a conductive substrate which consists of multiple parallel electrical circuits defined by parallel, low resistance, conductors on either side of a high resistance heating elements as shown in FIGS. 2A and 2B. When a current is driven through one of the parallel conductors through the high resistance heating element section returning to the other parallel conductor, that element heats up and volatizes the coating of cannabinoids previously deposited.

In one example, as shown in FIG. 3, the coated substrate can be converted by rolling the coated substrate to form a cylindrical structure having a spiral cross-section, when viewed from a longitudinal end of the rolled sheet.

The process of converting the flat extruded aluminum substrate, coated with its high concentration of herbal essences including but not limited to cannabinoids, and into a Vapor Cartridge can include rolling the substrate up into a spiral with the multiple parallel conductors outwardly exposed. Non-conductive spacers can create an open airflow tunnel through the Vapor Cartridge.

The spiral construction of the Vapor Cartridge as shown in FIG. 5 lends itself well to a continuous roll coating processing.

FIG. 7 depicts a physical Drug Delivery Device designed to implement the concepts described in FIG. 6. An important function of the drug delivery device is cleanly and efficiently extracting the herbal essences through use of a volatilizing chamber.

FIG. 8 shows a functional block diagram depicting how the exposed parallel conductors of the Vapor Cartridge match up to the contacts in the volatizing chamber. When, directed by the patient, a well-controlled current is driven through the selected section, volatizing the coating of herbal essences such as but not limited to cannabinoids.

SUMMARY

The present invention is directed to an alternative Vapor Cartridge utilizing an electrically conductible substrate coated with at least one or more herbal essences which is configured so as to manageably convert the one or more herbal essences into a vapor for inhalation into the lungs. An embodiment of the alternative Vapor Cartridge comprises a substrate of an electrically conductible material with conductor contacts and having coated on one side at least one herbal essence. The at least one herbal essence is coated on the substrate and includes such volatilizable essences as cannabinoids, hops, echinacea extracts, terpenoid extracts such as peppermint, spearmint, menthol, and similar volatilizable plant oils, gums, solids and similar essences. The electrically conductible substrate may be an electrically conductible metal or polymer having at least two low resistance conductor contacts positioned at opposite ends of, and conductively attached to, the substrate.

In preferred embodiments, in one alternative, the substrate is a flat sheet and in another alternative is a flat sheet configured with a mesh. The herbal essence is coated onto one surface of the flat sheet or is coated onto the mesh. When the mesh is configured with the substrate to become coated with herbal essence, the mesh is electrically conductive so that the herbal essence coated thereon can be volatilized. In an alternative configuration, the side of the sheet opposite side onto which the herbal essence is to be coated may be configured with an open mesh. The herbal essence is configured in this alternative configuration as a linear continuous layer on the surface of the sheet. The open mesh configuration of this alternative configuration enables airflow through the mesh to help carry the volatilized herbal essence from the side opposite the mesh side.

The Vapor Cartridge may be activated by application of electrical current to the conductors so as to heat the sheet and/or mesh between the conductors and volatilize the coating of herbal essence between the conductors. The current may be controlled so as to manage the temperature of the heated sheet section and/or mesh thereby managing the rate of volatilization of the herbal essence coating.

In a preferred embodiment of the Vapor Cartridge, the electrically conductive sheet and/or mesh may be sectioned by more than two conductors so as to provide separate portions of sheet surface between the multiple conductors. The separate portions of sheet surface and/or mesh may be coated with portions of the same or different herbal essence(s). The multiple conductors are present so as to section the sheet and coating and/or mesh and coating into separate sections. In a preferred embodiment, the sections of mesh are arranged so that multiple conductors of another sheet may fit in the spaces between the sections of mesh. In this embodiment, the conductor and corresponding mesh space arrangement enables fitting together multiple sheets in a stacked arrangement.

In a preferred embodiment of the sectioned coated sheets and/or coated mesh, a multiple number of conductors and a multiple number of sections of sheet and/or mesh coatings of herbal essences are present. The multiple numbers of conductors may be serially activated electrically so as to serially or co-serially volatilize the multiple sections of herbal essence coatings. In this manner, separate sections of a single herbal essence or different kinds of herbal essence may be serially, simultaneously or partially co-activated to volatilize and deliver to the user different sections of multiple herbal essences at different times or at the same time.

This Summary is intended to provide an overview of subject matter of the present patent application. It is not intended to provide an exclusive or exhaustive explanation of the invention. The Detailed Description is included to provide further information about the present patent application.

BRIEF DESCRIPTION OF DRAWINGS

FIGS. 2A and 2B disclose a prior art coated substrate with sections of herbal essence coatings.

FIGS. 11A, 11B and 11C disclose front and top views of the coated substrate with sections of coating but without mesh sections.

FIGS. 12A and 12B disclose the coated substrate with and without mesh, both having one section spanning the width of the coated substrate.

FIG. 13A discloses stacking to give stacked multiple coated substrates of FIG. 10A.

FIG. 13B discloses the stacked, multiple coated substrates of FIG. 11A.

FIGS. 17B, 17C and 17D disclose template use to form reservoir sections of herbal extract on a conductive substrate of FIG. 18B.

FIG. 17E discloses a process for production of the coating substrate of FIG. 18B from a liquid mixture of herbal essence in volatile solvent.

FIGS. 18A, 18B and 18C disclose detail of template/mask technique for preparation of a coated substrate.

DEFINITIONS

Figure 1:
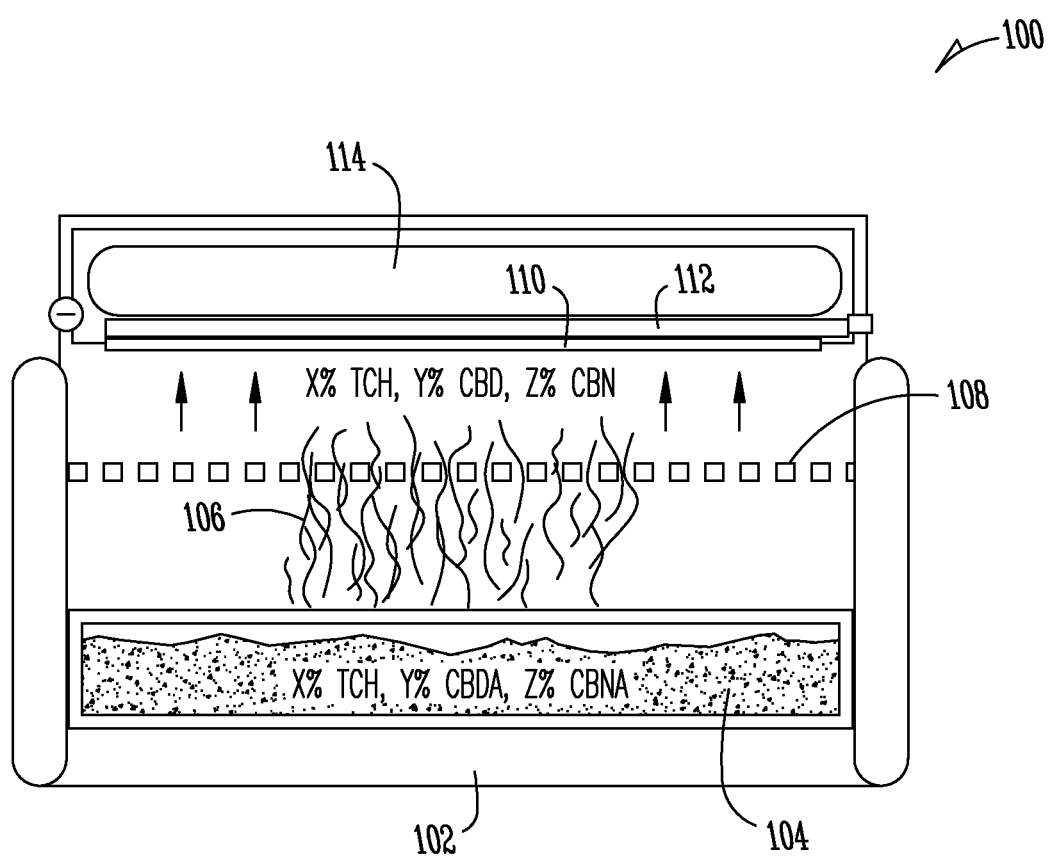
FIG. 1 discloses a prior art thermal distillation process.

The following terms as used herein according to the invention have the following meanings.

The terms "herbs" and "herbaceous plants" in the singular and plural are understood to mean all kinds of plants, funguses and algae that can contain or can produce essences that have a pharmacological, physiological, beneficial, sensory or other perceived or un-noticed but measurable effect on humans. The term herbaceous plant includes the stems, seeds, buds, roots, leaves, branches, bark, flowers fruit and all other parts of a plant. Preferably, these parts may be selected to provide only the plant part containing the desired herbal extract if appropriate. The term "herbaceous plant material" is understood to mean comminuted herbaceous plant material unless in context this term describes a whole plant.

As used herein pursuant to the invention, an "herbal essence" and/or "extract" and/or herbal substance are understood to mean an essence or derivative thereof obtained directly from an herbaceous plant or indirectly through synthetic methods applied to such plants and/or essences. An herbal extract or essence can be a solid, oil or liquid and can have a pharmacological, physiological, beneficial, sensory or other perceived or unnoticed but measurable effect on humans (e.g., an unnoticed but measurable effect may be, but is not limited to, lowering of blood pressure). In addition to the popular understanding that an herbal extract or essence is a flavor, taste and odiferous essence for use in foods, the term herbal extract(s) and related terms used herein include medicinal agents and essences, pharmacological agents and essences, and chemical agent, essences and compounds known or derived from any kind of plant, fungus or algae. Included also are semi-synthetic derivatives of such essences. The term "herbal extract(s) or essence(s)" includes any of the phrases "one or more herbal extracts/ essences" an "herbal extract or extracts or essence or essences", and herbal extract or essence, in other words, the singular herbal extract/essence and the plural herbal extracts/essences, i.e., multiple herbal extracts/essences.

As used herein according to the invention, the terms "volatilize" and/or "volatilization" are understood to mean vaporization of an herbal extract/essence from a material, which is either a liquid or a solid and can be vaporized to a gas or vapor phase. In an example, one or more herbal extracts/essences described herein may start as a solid or an oil and be heated such that the one or more herbal extracts/ essences vaporize. The one or more herbal extracts/essences may transition directly from the solid to the gas phase, a sublimation process, or the one or more herbal extracts may become a liquid and then vaporize to a gas. In an example, the one or more herbal extracts/essences described herein may be in a liquid or solid form prior to heating.

As used herein, the term "extracting techniques" mean obtaining a solid or liquid or oil herbal essence from herbaceous plant material by comminuting the plant material and either volatilizing the herbal essence from the plant material by heating under STP conditions and/or heating under vacuum conditions such as but not limited to vacuum distillation, or by extracting the herbal essence by wet chemical techniques applied to the comminuted plant material, wherein the wet chemical techniques involve one or more of solvent and/or mixed solvent combination with the plant material and which may utilize optional heat and optional pH variation to remove the herbal essence(s) from the comminuted plant material.

As used herein according to the invention, the terms "entrain", "entraining" and/or "entrainment" are understood to mean formation of a solid-gas mixture such as a solid-gas aerosol with air in which a solid, oil or liquid herbal extract is heated to an extent that it forms microparticles or microdroplets of liquid dispersed and/or mixed in a gas such as air. The common form of such a dispersion is a particulate-gas aerosol or a liquid droplet-gas aerosol. The entrainment does not require the herbal extract to vaporize into a gaseous state but instead to form an aerosol.

The term "may" in the context of this application means "is permitted to" or "is able to" and is a synonym for the term "can." The term "may" as used herein does not mean possibility or chance.

It is also to be understood that as used herein and in the appended claims, the singular forms "a," "an," and "the" include plural reference unless the context clearly dictates otherwise. The term "X and/or Y" means "X" or "Y" or both "X" and "Y". The letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and the right is reserved to revise the application or claims to refer specifically to any individual member or any subgroup of members of the Markush group.

The term "about" as used herein, when referring to a numerical value or range, allows for a degree of variability in the value or range, for example, within 10%, or within 5% of a stated value or of a stated limit of a range.

The term and/or as used herein means both of as in "and" and means either one of as in "or" and means a combination of such as but not limited to both at the same time. An example is "apply salt and/or sugar" to food which means apply salt and sugar to food sequentially or simultaneously, as well as apply one of salt or sugar, as well as combine the salt and sugar and apply both at the same time.

DETAILED DESCRIPTION

The present application is directed to a drug delivery system having a substrate coated with one or more essences that can be volatilized into a vapor for inhalation by a user. Essences serving as volatilization material include herbal essences obtained from comminuted material by extracting techniques. In an example, the one or more essences can include one or more herbal extracts of one or more herbaceous plants. In an example, the one or more essences can include at least one extract comprised of tetrahydrocannabinol (THC), cannabidiol (CBD), menthol, peppermint, hops, echinacea and similar herbal materials formulated as an oil or extract. Multiple coated substrates can be stacked together to form a Vapor Cartridge for use in a drug delivery device.

Prior Art Substrate

Figure 3:
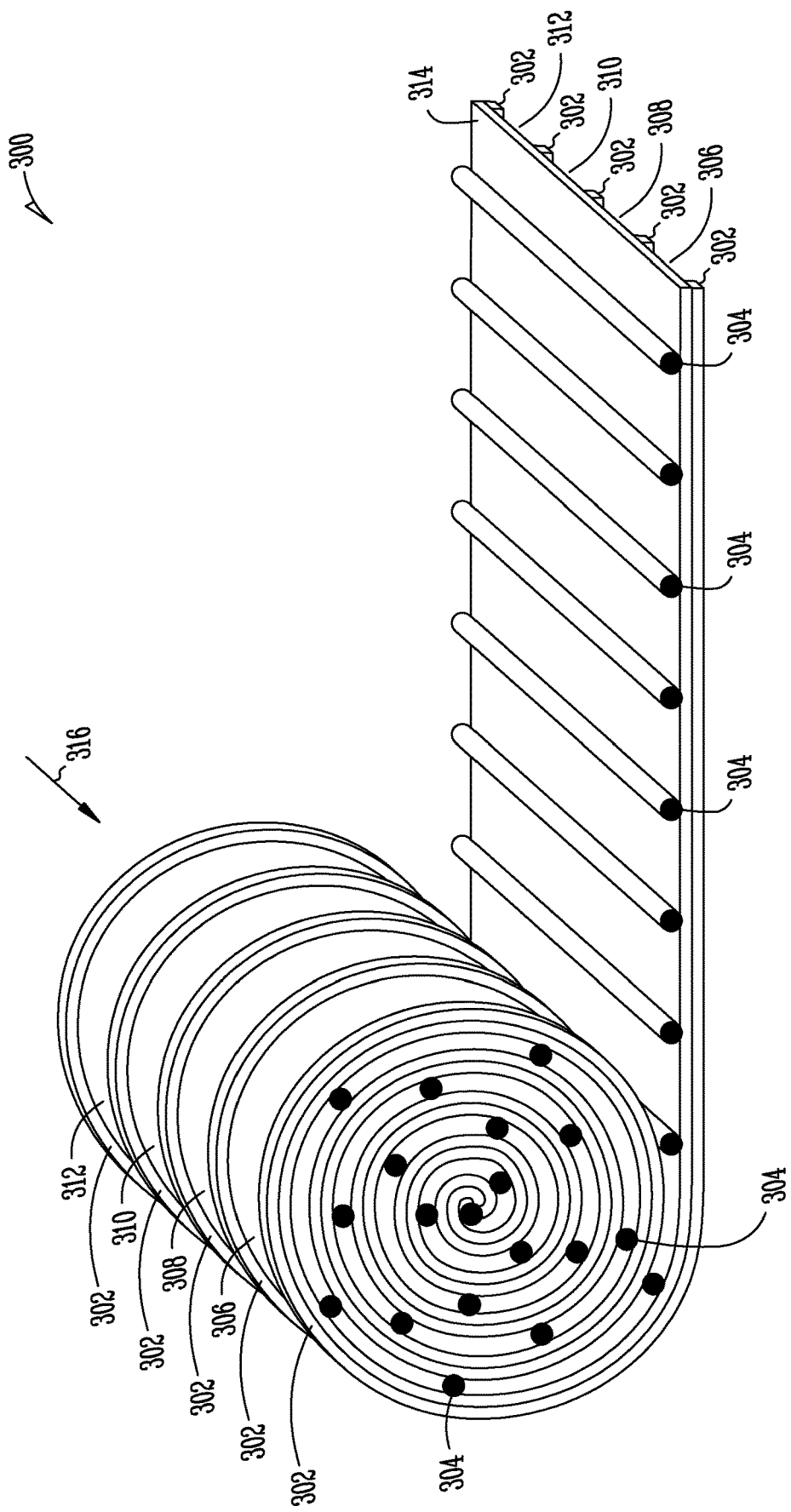
FIG. 3 discloses a prior art vapor cartridge

A prior art coated substrate configured as a roll is disclosed by FIG. 3. The process for forming the substrate with coating of an herbal essence such as a cannabinoid is illustrated by FIG. 1. The thermal chamber 100 contains source material as finely and uniformly chopped botanical herbs 104 with cannabinoids TCH, CBDA and DBNA illustrated as being produced from the herb. A controlled heat source 102 heats the botanical herb particulates 104 and vaporizes the herbal essences as vapors 106. A screen 108 captures any particulate floating on the current of vapor 106. Cooling bar 114 is maintained at a low temperature so as to keep substrate 112 (e.g. aluminum sheet) cold. Vapors 106 condense on the surface of cold substrate 112.

The substrate coated with herbal essence 200 produced by the technique shown in FIG. 1 is illustrated by FIGS. 2A and 2B. The aluminum substrate is divided into sections 204, 206, 210 and 208 by low resistance conductors 202. Herbal coating 218 forms a continuous coating on the substrate side opposite the conductors 202. Electrical current 222 (FIG. 2B) from source 214 powers electrodes 212 (FIG. 2A) and heats section 210 of the aluminum substrate. The heat volatilizes the section 216 of coating 218. Coated substrate 200 of FIG. 2A may be rolled into a vapor cartage 300 FIG. 3. Non-conductive spacers 304 on top of combined herbal essence coating and aluminum substrate 314. Low resistance conductors 302 divide the aluminum substrate into sections 306, 308, 310 and 312. Sections 306, 308, 310 and 312 are the same as sections 204, 206, 208 and 210 of FIGS. 2A and 2B.

Figure 4:
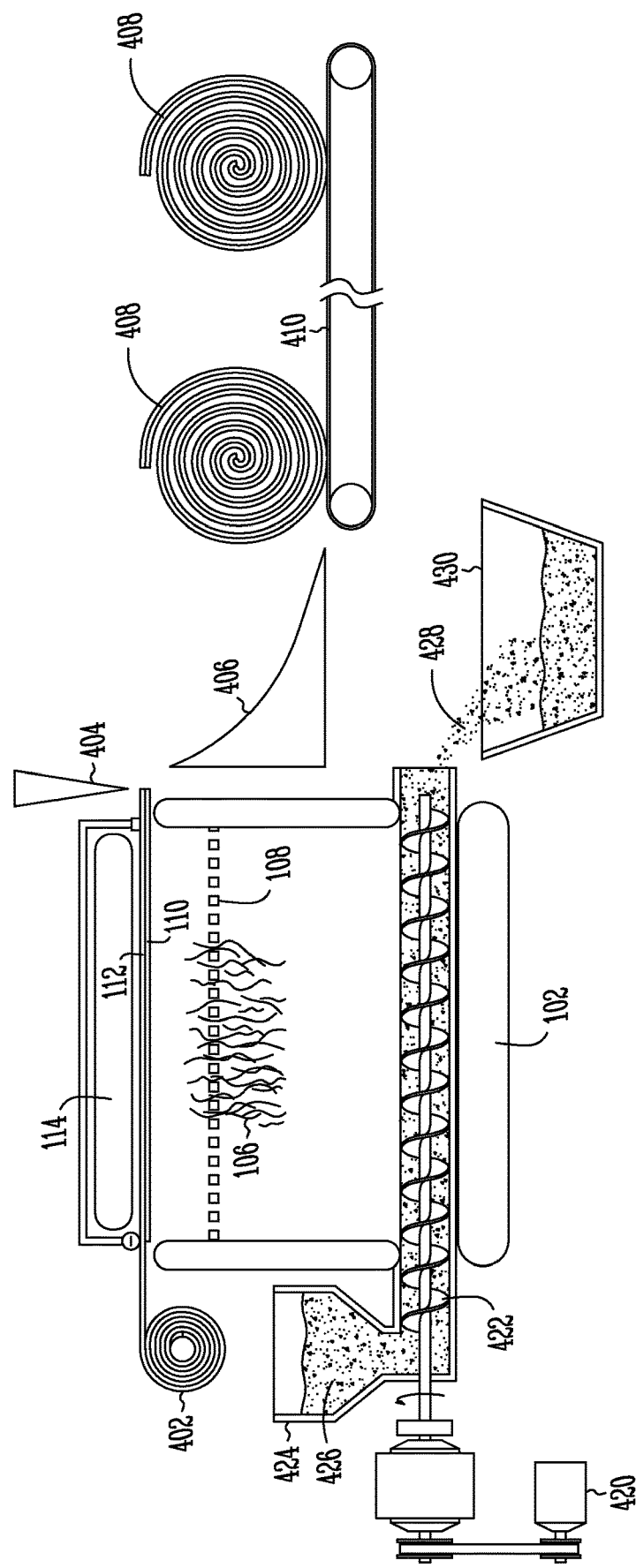
FIG. 4 discloses a prior art process for making the vapor cartridge of FIG. 3.

A fully automated process for producing vapor cartridge rolls of FIG. 3 is illustrated by FIG. 4. The motor 420 and gear box run a screw extruder 422 that comminutes herbal material 426 in hopper 424. Heat source 102 like that shown in FIG. 1 drives volatiles from the material 426 to produce herbal vapor 106 like that shown in FIG. 1. Screen 108 like that shown in FIG. 1 separates particulate floating in vapor 106 and vapor 106 is deposited as coating 110 on cooled metal substrate 112 like that shown in FIG. 1. Metal substrate 112 is produced from coil 402 and is cooled by cooling bar 114 like that shown in FIG. 1. Slicing bar 404 cuts sections of coated metal substrate 110/112 as the section is rolled into vapor cartridge 408. Vapor cartridge 408 is transported by conveyer 410 to a finished good inventory storage facility. Debris 428 from extruder 422 exits the extruder and is deposited in bin 430. Debris 428 may be used as fertilizer or as another source of nutrients for plants and/or animals.

Figure 5:
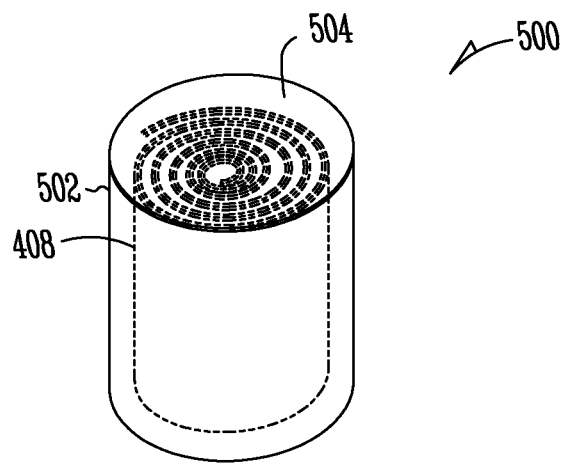
FIG. 5 discloses a prior art sealed vapor cartridge.
Figure 6:
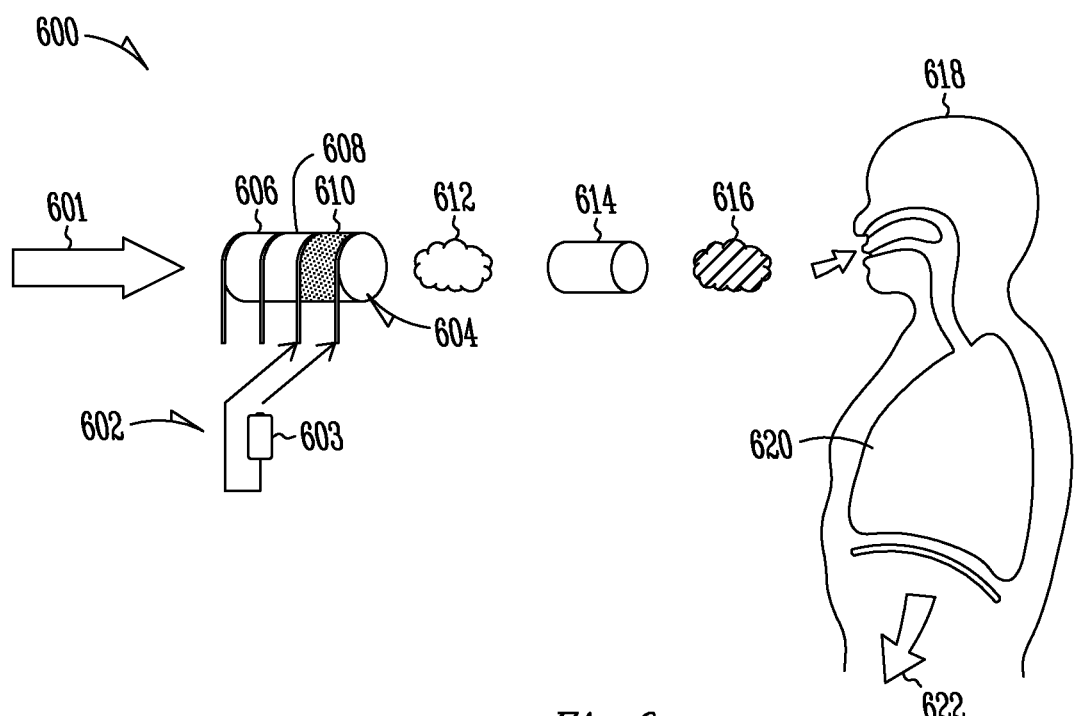
FIG. 6 discloses a prior art sketch showing the use of the vapor device.

The roll of Vapor cartridge 408 of FIG. 5 and as produced according to FIG. 4 may be packaged in a tamper proof seal 504 and packaged in outer packaging 502 of FIG. 5. Vapor cartridge 408 may be utilized for herbal vapor production as shown by idealized schematic 600 of FIG. 6. Section 610 of Vapor cartridge 608 like that shown as 408 of FIGS. 4 and 5 is heated through application of an electric current from conductors 602 and source 603 to produce an accurate does of vapor 612 carried on airflow 601. Optional vapors 614 may be added to vapor 612 for delivery of an appropriate dose 616 to patient 618 through inhalation into patient's lungs 620 by action of patient's diaphragm 622.

Figure 7A:
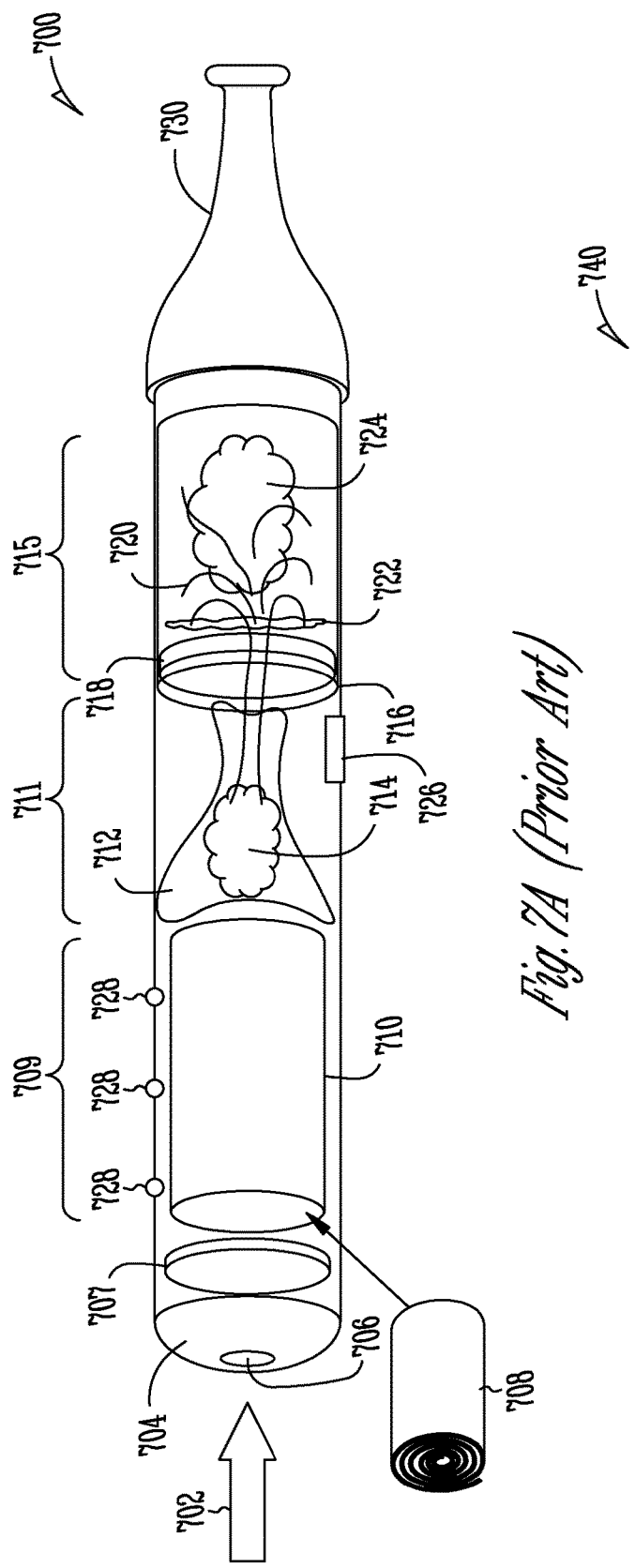
FIGS. 7A and 7B disclose a prior art drug (herbal essence) delivery device.
Figure 7B:
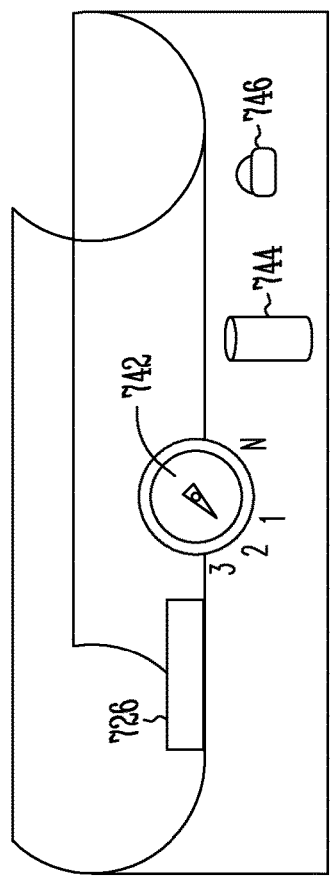
Figure 8:
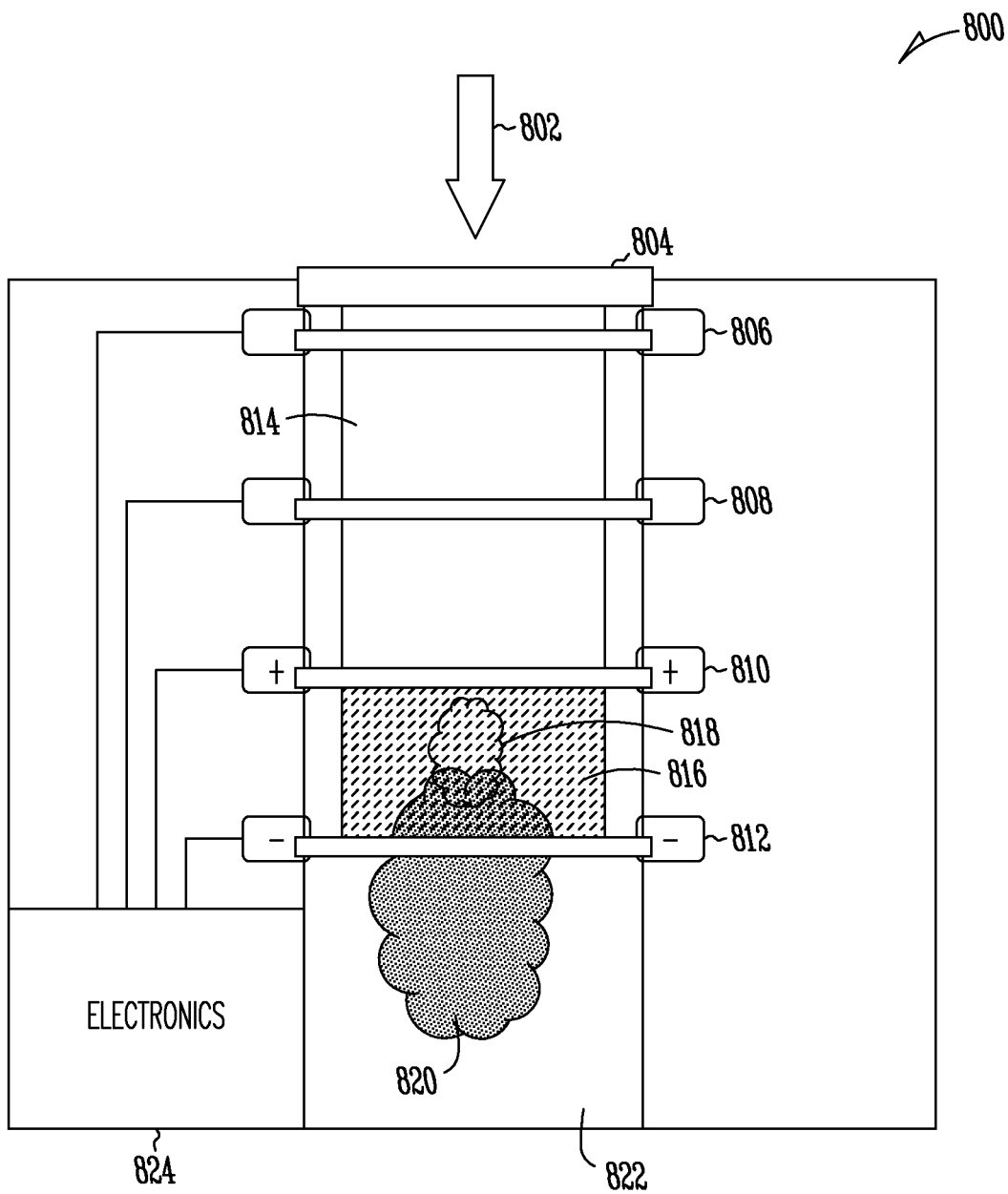
FIG. 8 discloses a prior art block diagram of a volatilizing chamber.

The functional elements of a prior art drug delivery device 700 of FIG. 7 include an air intake nozzle 704 for entry of air flow 702, air intake filter 707, vapor cartridge 708 inserted into vaporizing chamber 710 in reservoir chamber 709. Chamber 710 includes connections for the low resistance conductors of vapor cartridge 708 and the connection is indicated by LED indicators 728. Dose of vaporized herbal essence 714 is passed through vortex chamber 711 and venturi 712 and through misting ring 718 and injected mist 722 to produce herbal vapor 724 mixed with mist 720. the misted vapor 724 is drawn into the patient's lungs through mouthpiece 730. An expanded view of interface connector 726 with mist and controls is shown in FIG. 7B. The interface connectors 726 are connected to dose selection switch 742 and on/off control button 746. Mist reservoir 744 is connected by delivery tube (not shown) to misting ring 718. Functional block diagram 800 of FIG. 8 illustrates the operation of a device of FIG. 7. Electronics 824 delivers current to electrodes 810 and 812 to volatize coating 816 to produce vapor 818. Vapor 818 mixes with water mist to produce vapor 820 in mixing chamber 822. Electrodes 808 and 806 may be activated by electronics 824 to volatilize coating 814. Air intake filter 804 filters air 802 coming through air intake in filter 804.

Figure 9A:
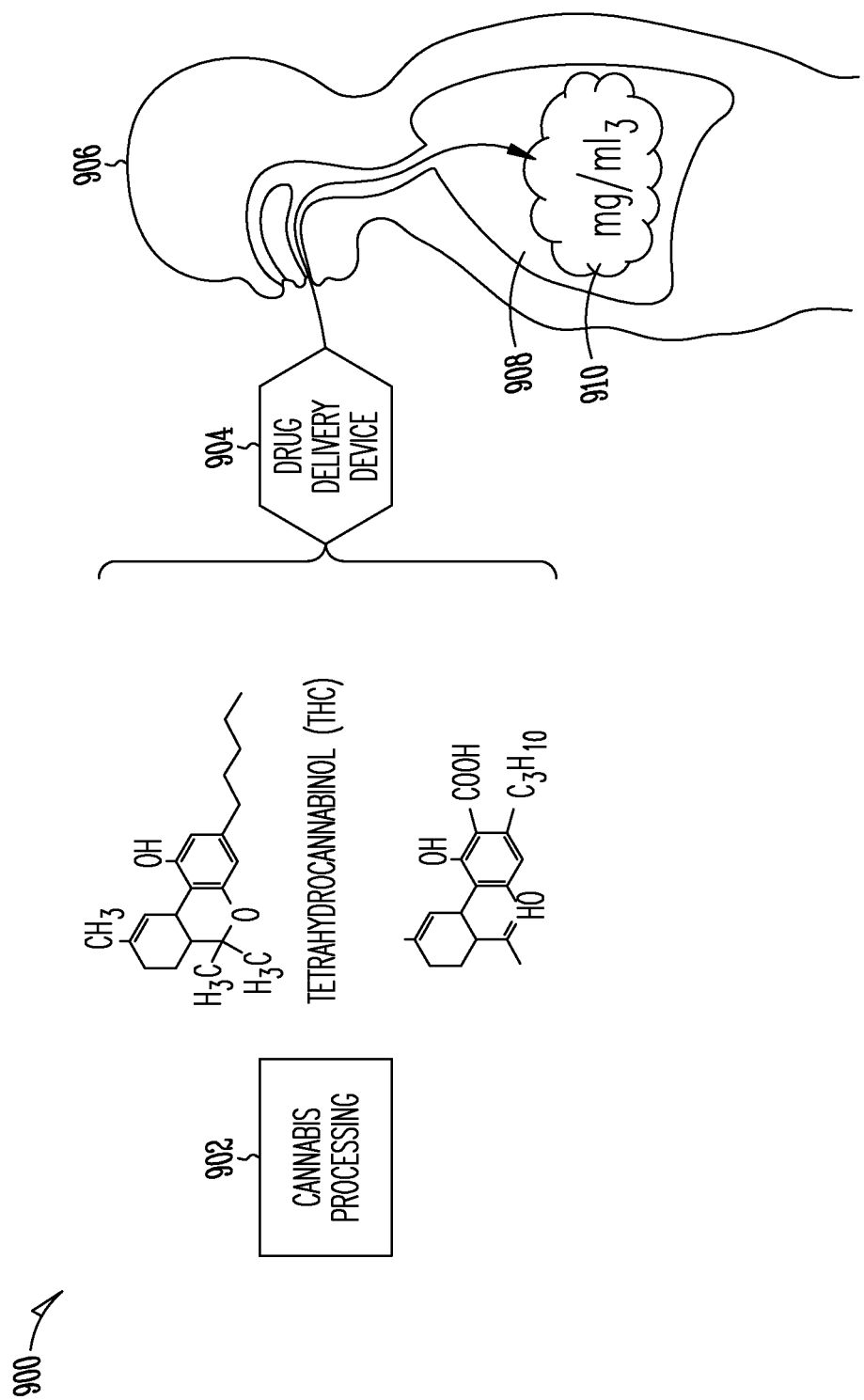
FIGS. 9A and 9B discloses the prior art process for conversion of plant material into herbal essence vapors for inhalation with cannabinoid essences being exemplified.
Figure 9B:
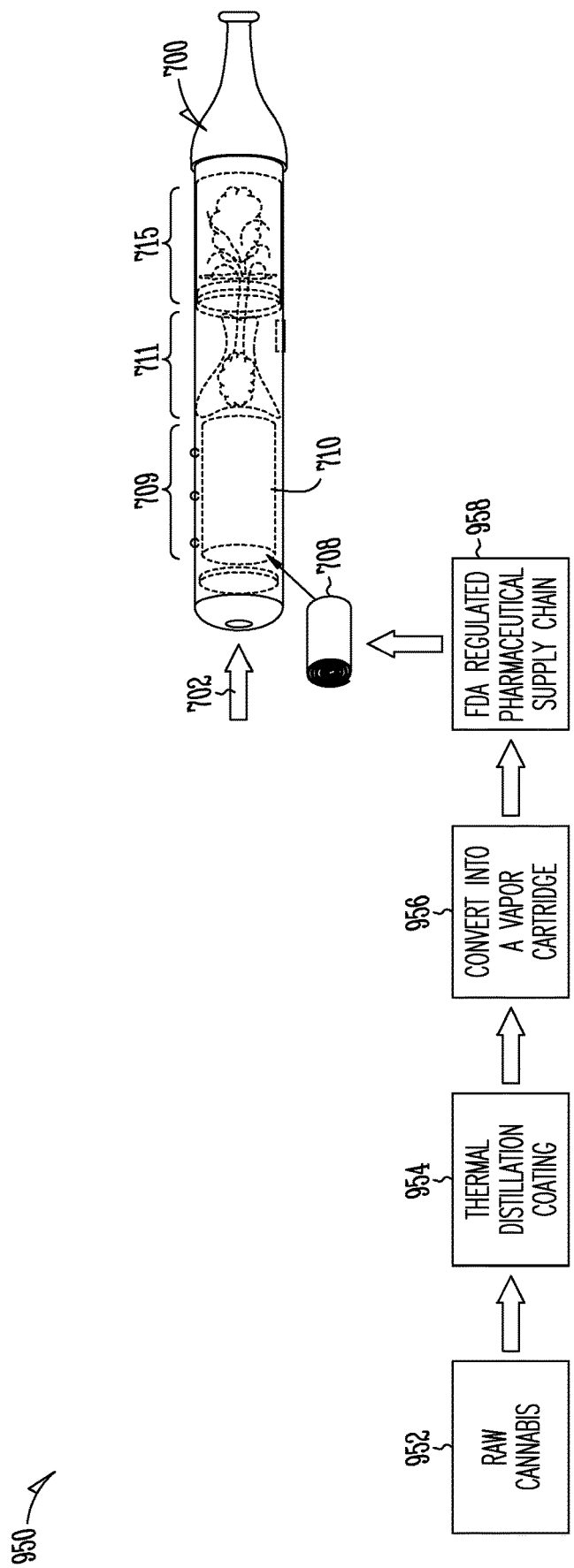

According to FIG. 9A, one of the herbal essences delivered by a drug delivery device 904 is THC from *cannabis* processing 902. The vapor from device 904 is delivered to patient 906 and into patient's lungs 908. The vapor 910 contains a controlled dose of TCH in mg per cc. The scheme for conversion of raw *cannabis* to vapor 910 is shown by FIG. 9B. Raw *cannabis* 952 is converted to by thermal distillation to a coating on a substrate 954. The coated substrate is converted into a vapor cartridge 956 regulated by the FDA 958. The vapor cartridge is loaded into a drug delivery device 700 as described above for FIG. 7A.

The stackable substrates according to the invention present an elegant design of coated substrate material that has a small volume but significant amount of herbal essence content. The stackable construction delivers a simple design of a coated substrate material that avoids the need for spacers and flexible conductors of the vapor cartridge roll of the prior art. Embodiments of the stackable substrates according to the invention are described in the following passages.

Stackable Substrates

Figure 10A:
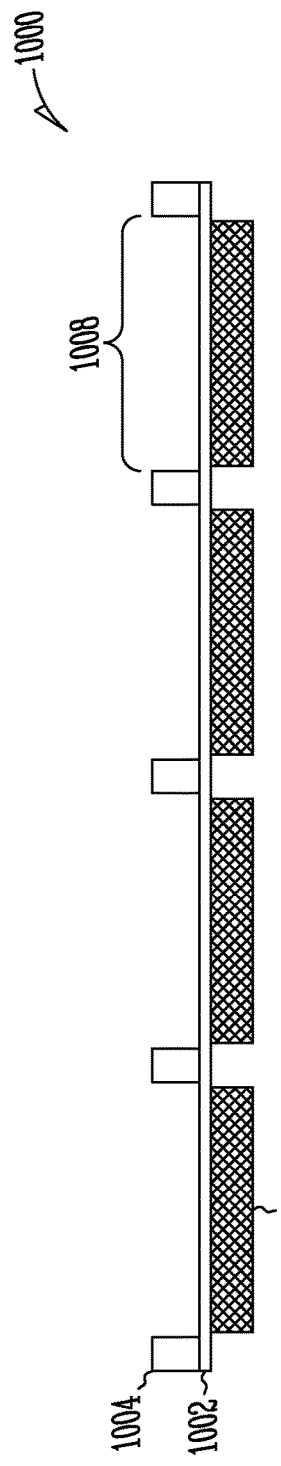
FIGS. 10A, 10B and 10C disclose front and side views of a coated substrate with mesh sections.
Figure 10B:
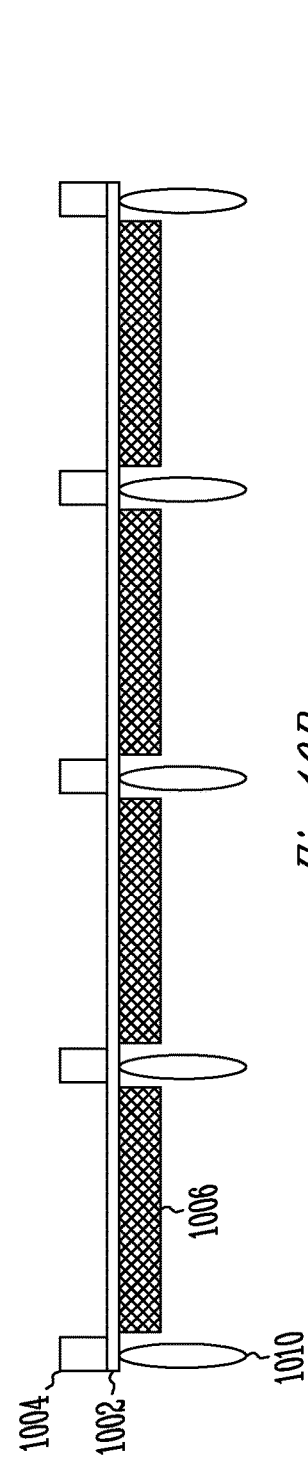
Figure 10C:
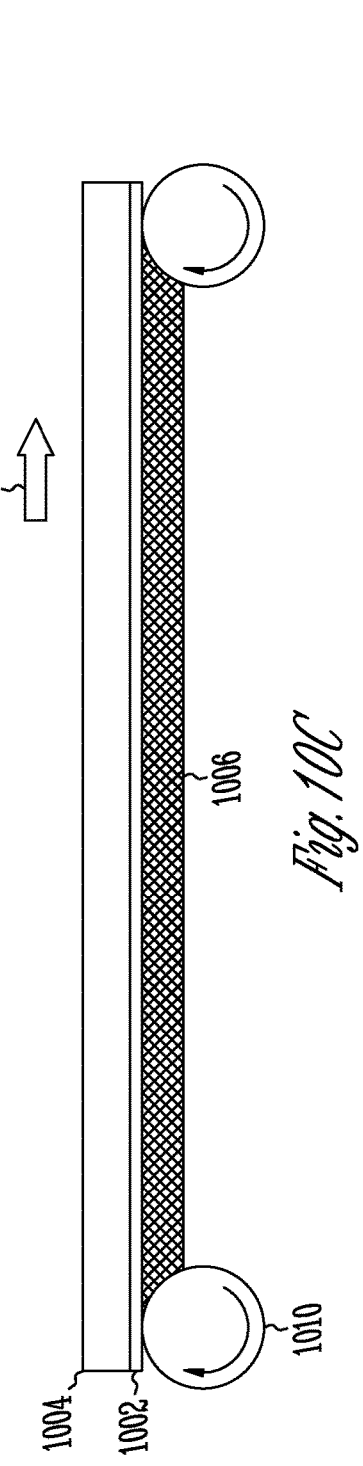

The Vapor Cartridge Technology comprises at least three components as shown in FIGS. 10-28. These three components comprise a substrate, an herbal essence coated on the substrate and conductor contacts at least at the ends or termini of the substrate. FIGS. 10A-D and 18A-C illustrate these components as a single article coated substrate, 1000, 1100 (FIGS. 10A, 11A) and 1800 (FIG. 18A-C). The single article coated substrate may comprise a substantially inflexible flat sheet of electrically conductive material 1002 combined with mesh 1006 as shown by FIGS. 10A-C. Alternatively, the single article coated substrate 1100 and 1802 FIGS. 11A and 18A-C may at least comprise a substantially inflexible, flat sheet of electrically conductive material alone shown as 1002 FIG. 11A and 1802 of FIGS. 18A-C. When the single article coated substrate includes a mesh as shown by FIG. 10A-C 1006, the mesh is attached to and combined with one side of the flat sheet 1002 and has a three-dimensional shape formed of filaments configured like a net forming the sides, bottom and top of an internally empty three-dimensional shape having a length, width and thickness. In a preferred configuration, the sheet 1002 and mesh 1006 are co-terminus so that their length and width dimensions are the same. One function of the mesh 1006 is to enable air flow appurtenant to the sheet 1002. Air flows through the openings in the net-like sides and bottom of the mesh. For the single article coated substrate configuration 1000 comprising the flat sheet 1002 combined with the mesh 1006, the herbal essence may comprise a film, layer and/or coating on the surface of the side of the sheet opposite the mesh, depicted by FIG. 10A with coating between conductors as section 1008 on side of substrate 1002 opposite mesh 1006. Alternatively, substrate 1000 may comprise a film, layer and/or coating on the side of the sheet 1002 with the mesh 1006 so that the film, layer and/or coating of herbal essence covers the filaments of the mesh 1006 and corresponding surface of the sheet 1002. When the substrate 1000 has a film, layer and/or coating of herbal essence on the mesh and sheet surface, the mesh net openings remain substantially open so that air flow is enabled through the mesh even though a film, layer or coating of herbal essence on the mesh filaments is present. When the substrate comprises the flat sheet alone as shown by 1100 and 1800, FIGS. 11A and 18B, the herbal essence may be a film, layer and/or coating 1120 and 1806 on the surface of one side of the flat sheet 1002, 1802. The coating 1120 1806 may be divided into sections separated by spaces 1130, 1808, FIGS. 11A, 18B or by non-conductive temporary dividers 1804, FIG. 18A, which may be cardboard or other nonconductive material.

The sheet 1002/1802 of the single article coated substrate 1000, 1100, 1800, FIGS. 10A, 11A, 18A, 18B, is electrically conductive so that its configurations as a sheet alone (e.g., 1100 and 1800 FIGS. 11A and 18B) and as a sheet-mesh combination (1000 FIG. 10A) are electrically conductive. Preferably, the sheet, 1002/1802 of 1100/1800, FIGS. 11A, 18B and sheet-mesh 1002/1006 of 1000 FIG. 10A, of both configurations is also thermally conductive and the thermal conductance quotient may be minimal to significant. In general, the sheet 1002/1802 of 1100/1800 and sheet/mesh 1002/1006 of 1000 should avoid being thermally insulative so that electrical resistance heating will enable volatilization of the one or more herbal essences coated on the single article substrate, 1000, 1100, 1800 of FIGS. 10A, 11A, 18B. The sheet 1002, 1802 of single article substrates 1100, 1800, FIGS. 11A and 18B and the sheet-mesh combination 1002/1006 of the single article substrate 1000, FIG. 10A may be comprised of a malleable metal including but not limited to aluminum or copper or may comprise an electrically conductive polymeric material formed of an electrically conductive composition of a heat conductive polymer containing conductible metal particulates or a polymer and metal sheet laminate. deformable or plastically deformable.

To provide electrically resistive heating of the single article coated substrate, the sheet 1002/1802 and sheet/mesh 1002/1006 may be electrically conductive such as by a metal including aluminum, copper or an electrically conductive organic polymer such as high temperature polyethylene, polypropylene or polycarbonate or polyacrylate or similar polymers preferably doped to make the polymer(s) electrically conductive, as well as inorganic (e.g. silicone) polymers. The resistive potential of the sheet and sheet/mesh will be sufficient to generate heat and volatilize or cause air flow entrainment of the herbal extract(s).

Preferably the sheet and sheet/mesh configurations are constructed of aluminum.

Figure 13C:
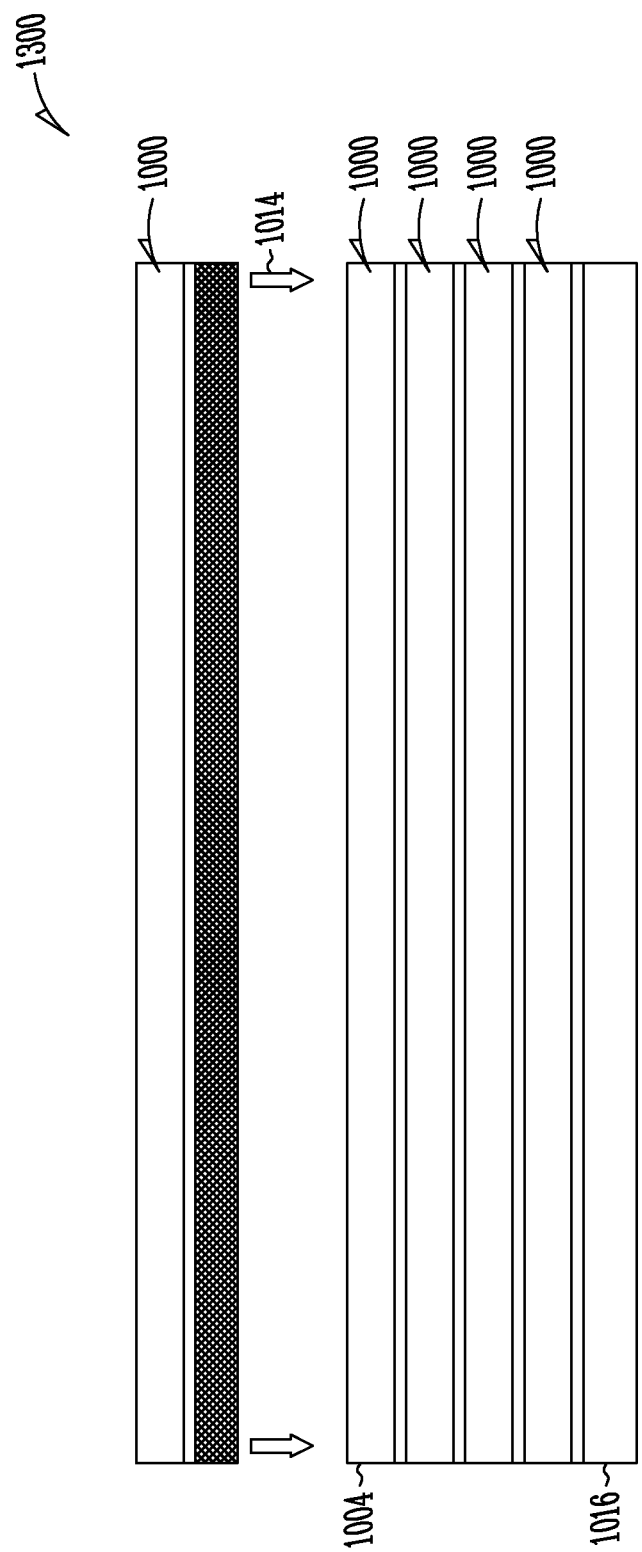
FIG. 13C discloses the side view of stacking to give stacked multiple coated substrates of FIG. 10A.

The single article coated substrate embodiments 1000, FIG. 10A and 1100 FIG. 11A also comprise conductors (1004, FIG. 10A, 11A) that are formed of low electric resistance material such as copper or aluminum or other conductive metal or conductive polymer. The conductors are positioned on and connected to the sheet 1002 or sheet-mesh 1002/1006 so that an electric current applied to a pair of conductors will pass through the sheet or sheet-mesh and these features of the sheet or sheet-mesh are sufficiently resistive so that the current passing through these features will generate heat. The conductors can be attached to the sheet or sheet-mesh prior to coating with the one or more herbal essences to form the single article coated substrates. The conductors can be mill pressed into appropriate shapes along with mill pressing or molding the flat sheet feature of the substrate 1000, 1100 such that the conductors are thicker portions of the sheet feature of the substrate. Alternatively, separate low resistance material can be shaped into separate conductors 1004 and may be attached to the sheet feature 1002 of the substrate 1000 and 1100 by spot welding, soldering, adhesive bonding with electrically conductive adhesive, mechanically clamping and/or by otherwise forming an electrically conductive bond between the conductors 1004 and the sheet feature 1002 of the substrate 1000 and 1100. For single article coated substrate 1800, conductors comprise a separate part described below. The separate conductors mate with conductor contacts of the spaces 1808 of 1800 FIG. 18B. The conductor contacts at spaces 1808 may be exposed sheet surface 1802 or may be conductor material described above formed into space 1808 fitting conductor contact shapes with slight to moderate thickness but less than the coating 1806 thickness. These conductor contacts may be bonded to the sheet at spaces 1808 as described above. The conductors and conductor contacts function as electrodes to electrify the sheet 1002 or the sheet-mesh 1002-1006 configurations of the substrate 1000 and 1100 so that electrification of the substrate 1000 and/or 1100 through the conductors and separate conductors with the conductor contacts will heat the coating and volatilize the one or more coated herbal essences to form an aerosol for inhalation. The conductors of substrates 1000 and 1100 may also function to separate multiple stacked, coated substrates 1000 and 1100 and provide structural support to the stacked substrates as depicted in FIG. 13A for a stack of substrate 1000's and FIG. 13B for a stack of substrate 1100's. The stacks of FIGS. 13A and 13B are supported by a non-conductive frame 1016 on which the stacks rest. For coated substrates 1100 (no mesh) and optionally for coated substrates 1000 (with mesh), the lengths of the conductors are preferably adjusted so that the stack of substrates has spaces between the layers of substrates thus providing air channels through and between the stacked substrates.

The substrate constructed with a flat sheet (FIG. 11A, FIG. 18B) or with a flat sheet-mesh combination (FIG. 10A) may be segmented into separate sections (FIG. 10A, 1008, FIG. 11A 1120 and FIG. 18B, 1806) and the sections may comprise the same or different herbal essences. The sections are defined by conductors (FIG. 10A, 1004, FIG. 11A, 1004 or conductor contacts (FIG. 18B, 1808) spaced at intersections of the sections. While the sheet 1002 (FIGS. 10A and 11A) and 1802 (FIG. 18B) is a contiguous form and can conduct current from one end to the other, multiple conductors 1004 and/or conductor contacts (1808 with contacts) defining sheet sections are arranged so that current will flow from one conductor/contact to the adjacent conductor/contact at the other side of the same section. In this manner, only the sheet section between the two electrically connected conductors/contacts will be heated. When the substrate is a sheet-mesh (FIG. 10A, 1002/1006), the mesh is physically divided into sections corresponding to the sheet sections so that the mesh sections are not capable of independently conducting a current through all sections (FIG. 10A). Individual mesh sections are transmissively connected to the sheet sections so as to enable current to pass through an individual mesh section when conductors of the corresponding individual sheet section carry current. This configuration is shown in FIG. 13A. When stacked as shown in FIG. 13A, the conductors of a lower sheet-mesh intersect the mesh section spaces of an upper sheet mesh. The lower sheet mesh conductor electrically connect with the corresponding mesh sections of the upper sheet-mesh thereby providing a second pathway for current conduction.

As a minimal embodiment of a substrate configuration comprising a flat sheet alone with two conductors, the entire sheet surface may be coated with one or more herbal essences between the conductors. This configuration is shown as FIG. 12B, 1201, with conductors 1004 only at the ends of sheet 1002 and the herbal coating 1020 as a continuous coating on the side opposite the conductors. In a preferred embodiment of the substrate shown as FIG. 12A, 1200 with two conductors 1004 only at the ends of sheet 1002 and a contiguous mesh 1006 without intervening spaces, the entire sheet surface opposite the mesh may be coated with one or more herbal essences, or the entire mesh and corresponding sheet surface may be coated with one or more herbal essences. In more preferred embodiments of the substrate comprising a flat sheet-mesh and multiple conductors segmenting the substrate into separate sections (FIG. 10A), each section may be coated with one or more herbal essences. The section coatings may be on the sections of the flat sheet side opposite the mesh sections or may be on the sections of mesh and corresponding flat sheet. The section coatings of one or more herbal essences are positioned between the adjacent conductors. When functioning as a support for the coating, the mesh at least in part has herbal essence coating the filaments and between the filaments of the mesh; however, at least a part of the net openings of the mesh are open or not closed with herbal essence film so that air flow through the mesh is enabled. As mentioned above, the sections of mesh in the embodiments of multiple sections of substrate comprising the flat sheet-mesh configuration (FIG. 10A) have open spaces between the mesh segments which align with the conductors of a lower multiply sectioned sheet-mesh configuration (FIG. 13A). The alignment is adapted to enable stacking of multiple sheet-mesh configurations so that the multiple conductors of a lower sheet-mesh fit the open spaces between mesh sections of an upper sheet-mesh. The sheets can be stacked together as shown in FIG. 13A to form the Vapor cartridge of FIG. 15.

The embodiments of the present invention incorporate a substrate that is not substantially bendable or twistable, has moderate rigidity and yet has some low degree of flexibility. The substrate 1000, 1100, 1200, 1201, 1800 (FIGS. 10A, 11A, 12A, 12B and 18B) can be constructed as substantially flat, regular form sheets 1002, 1802 (FIGS. 11A, 12B, 18B) or sheet-mesh configurations (FIG. 10A) and in a preferred embodiment can be rendered stackable with other substrates to form a Vapor Cartridge with conductors and heating elements as described above. This substrate construction, 1000, 1100, 1200, 1201, 1800 (FIGS. 10A, 11A, 12A, 12B, 18B) renders the Vapor Cartridge significantly less flexible and with greater material strength than that of a substrate that is highly flexible and can be used in the spiral construction (FIG. 3). The flat, low flexibility substrate of the stackable Vapor Cartridge substantially prevents flexing of the herbal essence coating on the multiple substrates and thereby substantially prevents cracking and/or flaking of the coating. In contrast, earlier designs of cartridges calling for a spiral construction (FIG. 3) necessitated a flex characteristic of the herbal essence coating and can lead under certain circumstances to flaking, dislodging and laminate separation of the coating and spiral substrate. In such circumstances, the laminate separation may lead to inappropriate and/or incomplete volatilization of the herbal essence coating when heated.

A substrate embodiment formed with coatings of more than one herbal essence is illustrated by FIG. 10A. The side view, FIG. 10C, indicates movement of the substrate through a coating process. The circles 1010, FIG. 10C, represent wheels moving the substrate through a coating device. A composition of an herbal essence in volatile solvent such as ethanol produced as described in the above referenced Canadian patent may be applied to a mesh section 1006 and sheet 1002 of the lower part of the substrate 1000 through a spray nozzle, a brush or other flowable composition application device. Warm air passed through the mesh as the composition is applied and will evaporate the volatile solvent and leave a coating of herbal essence on the mesh section. Referring to the back/front view, FIG. 10B, this process would apply the herbal essence to the mesh segment 1006 at the left side of the substrate. Use of similar simultaneous applications using multiple application devices would apply the same or different herbal essences to the other three mesh sections of the substrate shown in the back/front view, FIG. 10B. Instead of application of the herbal essence composition to the underside of the substrate, multiple application devices may also be employed to apply multiple herbal essence compositions to the top sections of the substrate of FIG. 10B between conductors 1004. With these application techniques applying multiple herbal essence compositions to the top sections or bottom sections of the substrate 1000 so as to coat sections of the flat sheet 1002 or sections of the mesh 1006 respectively, a substrate 1000 with multiple herbal essences coated thereon may be produced.

FIG. 13A illustrates the multiple combination of single article coated substrates 1000 as segmented sheet-mesh configurations with conductors produced as described according to FIG. 10A and shows how they mate together to form stackable substrates. FIG. 13B illustrates the multiple combination of single article coated substrates 1100 as segmented sheet configurations (no mesh) with conductors produced as described according to FIG. 11A. Conductors 1004 can be formed as part of the conductive sheet 1002 or can be attached to the conductive sheet 1002. In an example for coated substrate 1000 (FIG. 10A), a conductive mesh material 1006 may be attached to an underside of the conductive sheet. As discussed above, one or more herbal essences can be coated onto the substrate 1000 by application of a composition of herbal essence and volatile solvent onto sections of the conductive sheet or onto sections of the conductive mesh.

Figure 14:
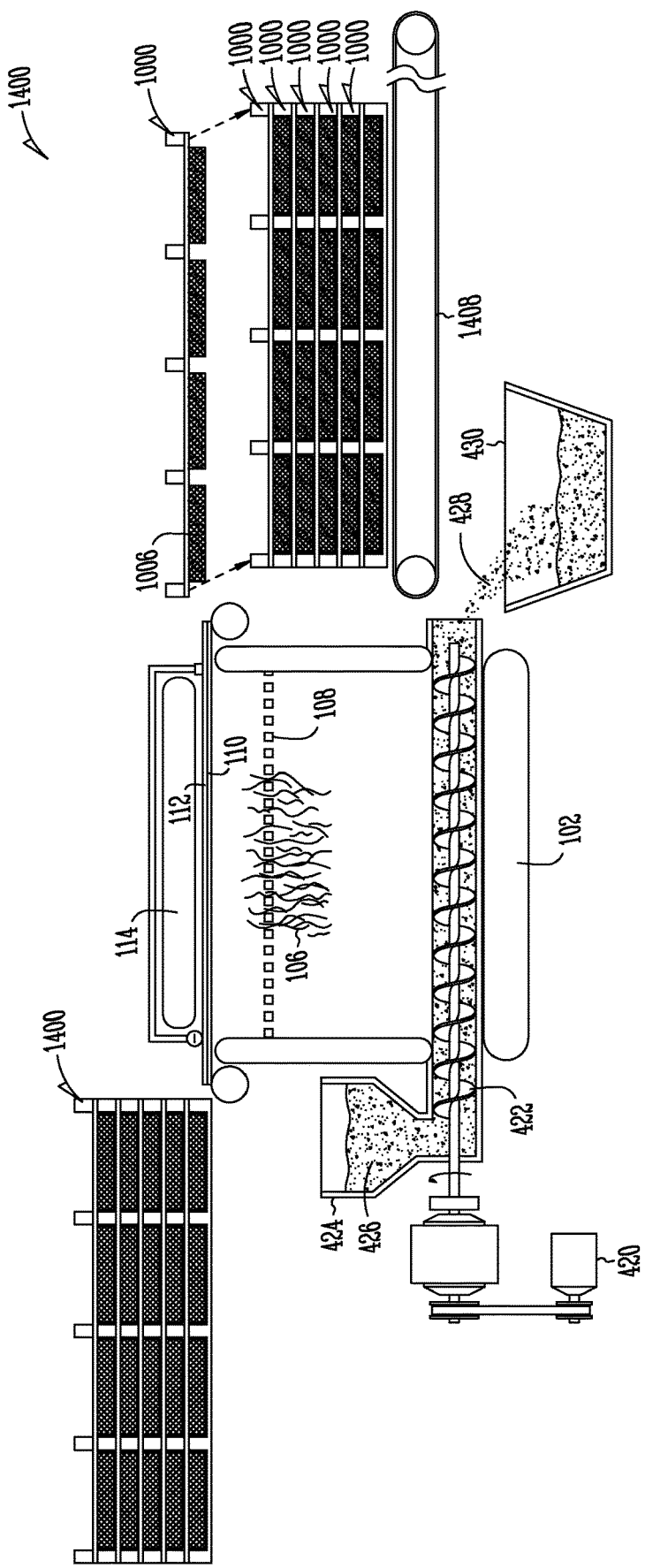
FIG. 14 discloses a vaporization process for coating mesh sections of a substrate with mesh sections.

Embodiments of the substrate 1000, 1100, 1800 including the flat sheet with and without mesh 1006 (FIGS. 10A, 11A, 18B) can be thermally conductive in addition to electrically conductive. Preferably, both properties apply to these embodiments of the substrate. With this preferred embodiment, the volatilization of the coating by resistive heating of the sheet and/or sheet-mesh readily occurs. In addition, these preferred embodiments of the substrate can be readily prepared with the heat volatilization technique for removing herbal essences from comminuted plant material as described in the above referenced U.S. patent. These embodiments of the substrate can be chilled by a cooling bar and placed in contact with one or more vaporized herbal essences thus allowing the one or more herbal essence vapors to condense onto the appropriate features of the substrate as shown in FIG. 14, illustrated with the sheet-mesh configuration 1400 before coating with herbal essence. Feeder hopper 1300 delivers a segmented substrate/mesh 1400 to the vaporization/cooling device in which extruder 422 moves comminuted herbal material 426 past heat source 102. Herbal vapors 106 rise through screen 108 and are deposited on substrate/mesh 1400 which are cooled by cooling part 114. A number of resulting substrate/mesh with coated herbal essences 1000 are stacked together and moved by conveyer 1408 to the finished goods repository. Herbal waste material 428 is deposited in bin 430 to agricultural use.

Figure 15:
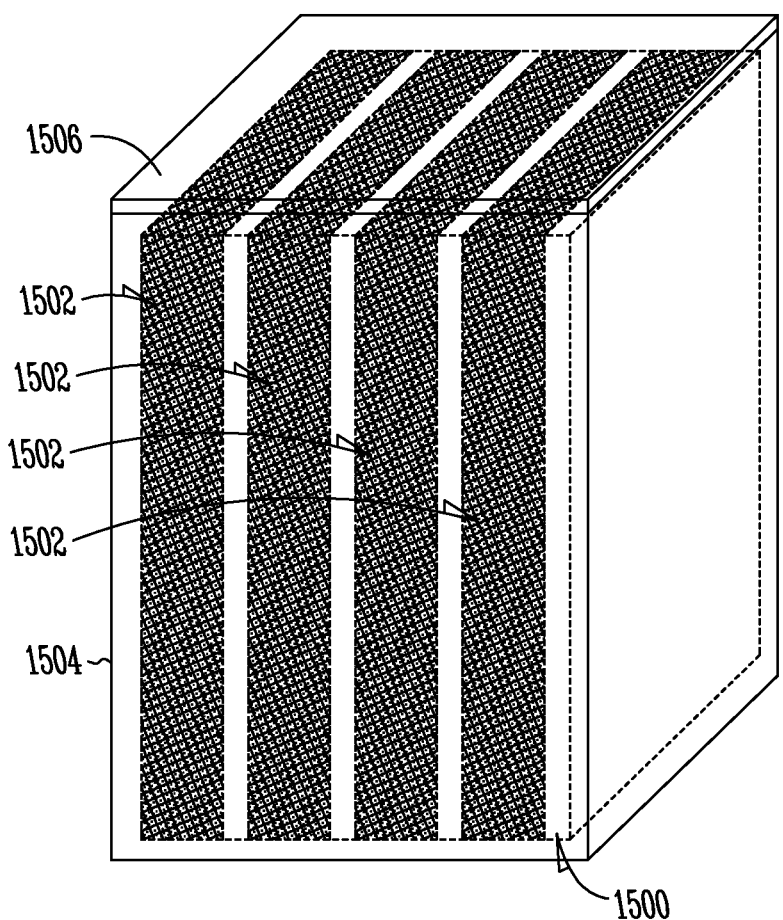
FIG. 15 discloses a stacked vapor cartridge.
Figure 16:
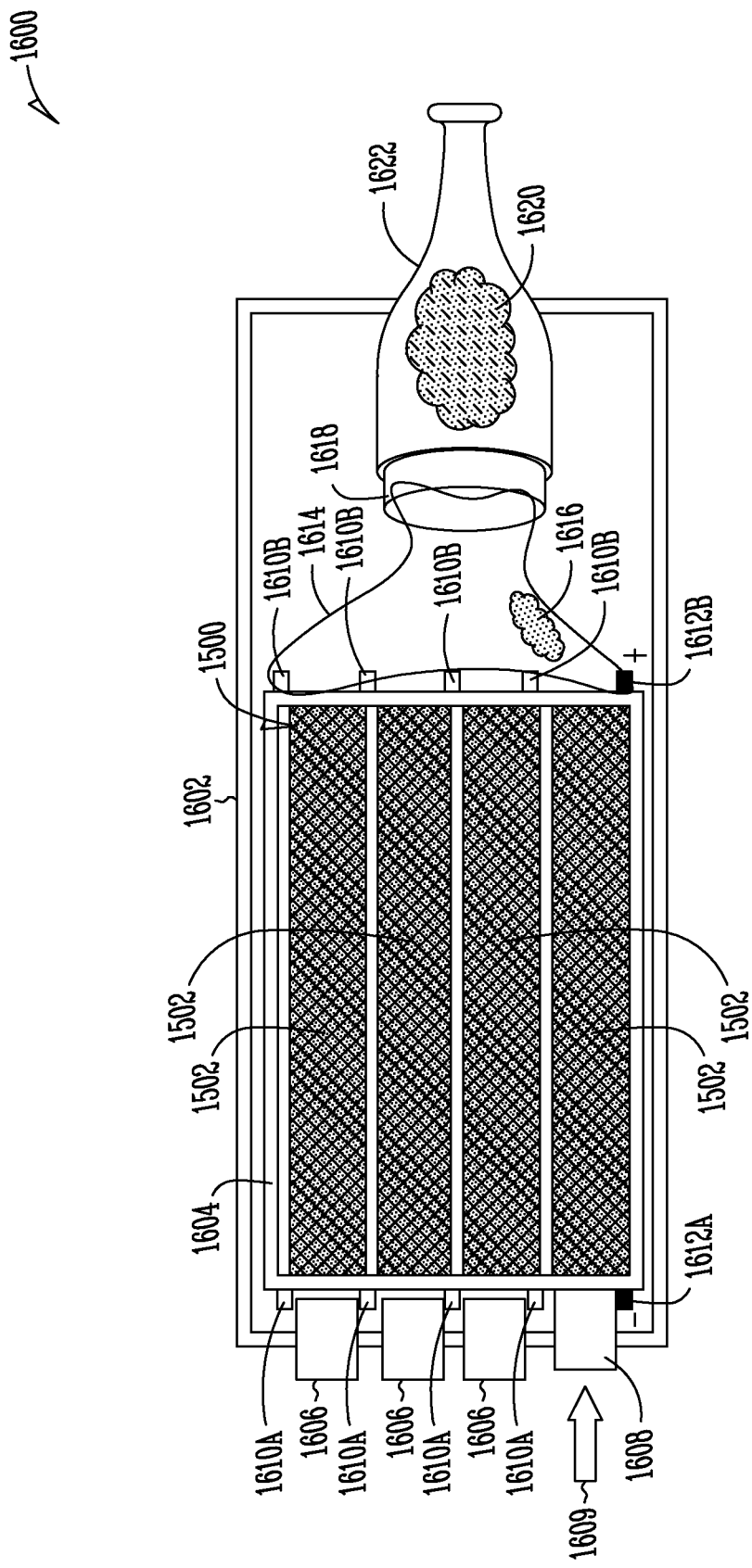
FIG. 16 discloses a delivery device with vapor cartridge of stacked coated substrates according to FIG. 15.

The stacked, coated substrates 1000 as depicted in FIG. 13A respectively may be formed into a Vapor Cartridge 1500 depicted in FIG. 15 as packaged in outer packaging 1504 with removable seal 1506. The conductors preferably run parallel to the long axis of the Vapor Cartridge. This configuration enables appropriate electrical connection when the Vapor Cartridge is inserted into an herbal essence delivery device 1600 as shown by FIG. 16 so that the stackable Vapor cartridge 1500 and the delivery device 1600 have electrical contacts 1620B and vapor cartridge conductors 1610A arranged to be parallel to the axis defined by the air intake nozzle 1608/1606/and the removable mouth piece 1622. Moreover, the coated substrates of the Vapor Cartridge 1500 are stacked in an orientation transverse to the direction of the air flow through the Vapor Cartridge. This orientation enables the air flow 1609 to move directly through the stack air channels 1502 that run parallel to the axis defined by the air intake 1608 and the removable mouthpiece 1622. Applying a current between conductors A and B (1612A, 1612B) of the stackable Vapor Cartridge 1500 causes current to flow through the bottom section of the Cartridge indicated by the arrow for air flow 1609. The current heats this section of the Cartridge and volatilizes the herbal essence of the bottom section. The herbal essence delivery device can be reused with one or more replacement vapor cartridges after the first Vapor Cartridge is used and discarded.

The herbal essence delivery device 1600 can include air intake selectors 1608/1606 which can facilitate selective air flow 1609 through the Vapor Cartridge 1500 and selective activation of the various heating sections 1502 of the coated substrate. Thus, the herbal essence delivery device can provide segmented heating and segmented volatilization of the one or more herbal essences on the coated substrate. The control system of the herbal essence delivery device can control opening and closing the air intake selectors 1608/1606 depending on whether the sections of the coated substrate 1502 are to be heated at the same time (causing the one or more herbal essences on adjacent sections to be volatilized at the same time) or if the sections of the coated substrate 1502 are to be sequentially volatilized.

Stackable Substrates in a Reusable Cartridge

Another embodiment of the Vapor Cartridge is directed to a substrate coated with one or more herbal essences that can be inserted as a single article into an herbal essence delivery device (FIGS. 17, 18). Multiples of the single article substrate with coating may also be stacked together in the in an herbal essence delivery device to form in place the stacked, coated substrates in the device. Preferably, the device is also configured for use of a single article of a substrate coated with one or more herbal essences. The construction of the single article coated substrate lends itself to efficient production of substantial quantities of one or more herbal essences coating on the substrate.

The single article substrate 1700 FIG. 17D coated with one or more herbal essences comprises a flat sheet 1702 to be coated on one side with separated sections 1708 of one or more herbal essences. In this embodiment of aspects of the invention, no mesh is included as a feature of the substrate. The one or more herbal essences may be present on the substrate 1702 as separated sections 1708 (FIG. 17D). The separated sections accommodate development of multiple different herbal essences on a single flat sheet 1702. The separations 1708 between sections 1710 of one or more herbal essences are free of any herbal essence so that the surface of the flat sheet 1702 is exposed at these separations. The separations 1708 and sections 1706 are best shown as 1808 and 1806 respectively on FIG. 18B.

The separated sections 1706 of coated substrate (FIG. 17D) with one or more herbal essences are produced through use of a mask 1704 (FIG. 17C) that isolates the sections and provides blank spaces between the sections. The mask 1704 (FIG. 17C) may be applied as a template 1704 to the flat sheet 1702 (FIG. 17C) wherein the mask outline is divided into sections 1706 by rows 1706 of template material 1710 (FIG. 17C). The template material has a thickness that enables ready filling of the corresponding sections with one or more herbal essences. The template outline form and thickness enables construction of layers of herbal essences 1706 (FIG. 17D) adapted to have at least some depth and preferably significant depth.

The template may be a support form 1704 (FIGS. 17B, 17C) on which the flat sheet 1702 is placed for coating with one or more herbal essences. A preferred construction of the support form provides the template outline with the outline rows 1710 defining the sections 1706 for herbal essence coatings (FIG. 17C). In one embodiment, the support form may be a permanent or semi-permanent part of the apparatus for coating the one or more herbal essences onto the flat sheet embodiments of the substrate. In another embodiment, the template may be temporarily affixed to the flat sheet and the flat sheet with template transported through the coating apparatus for applying the one or more herbal essences. Application of the one or more herbal essences to sections 1706 of the flat sheet 1702 defined by the template 1704 produces the coated flat sheet removably connected to the template (FIG. 17C). The template may be separated from the coated sheet/template combination to provide the single article coated substrate 1700 shown in FIG. 17D. The template may be repeatedly used to form additional flat sheets coated with separated sections of one or more herbal essences.

Figure 17A:
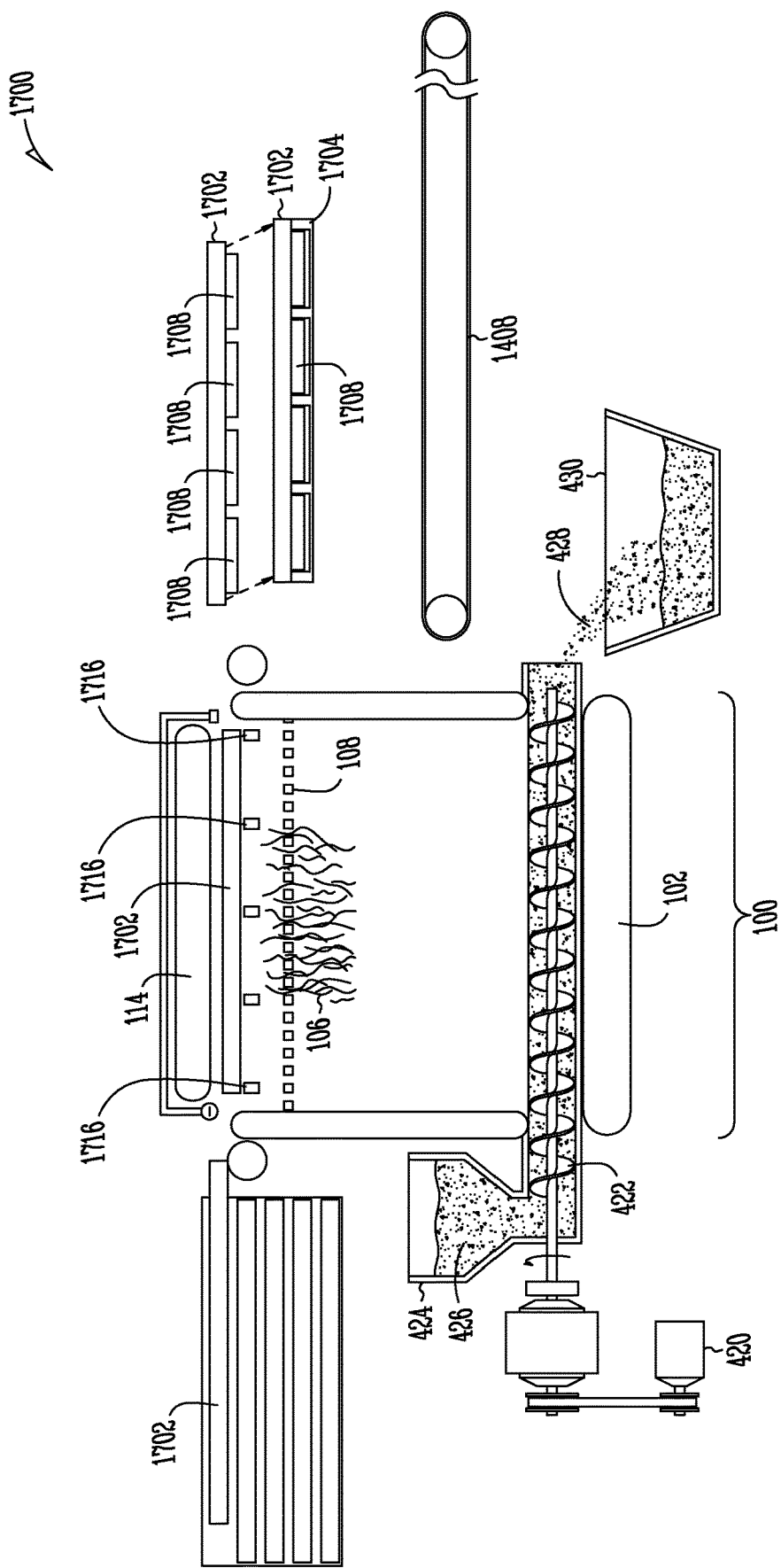
FIG. 17A discloses a process for production of coated substrate with coating sections and a holding frame, no mesh.

When the template is a permanent or semi-permanent part of the coating apparatus, template is a support platform associated with the coating apparatus. For example, as shown in FIG. 17A, the template 1716 can be a permanent part of the thermal distillation chamber 100 and can be formed of a thermally stable material such as ceramic. With this arrangement of the template 1716 permanently attached to the chamber 100, the flat sheet 1702 with separate sections of one or more herbal essences 1706 may be removed from the chamber 100 and another flat sheet 1702 moved into place on the template support form 1716 of the chamber 100. The coated substrate 17000 may be placed on a temporary support form 1704 for transport on conveyer belt 1408 and storage.

In another embodiment, the template 1704 is disposable, is affixed to the flat sheet 1702, and passes with the flat sheet through the coating apparatus to provide the coated substrate 1700 with attached disposable template also acting as a support form (FIG. 17C). The attachment between template 1704 and flat sheet 1702 (FIG. 17C) may be accomplished by a non-tacky gum or a suction feature of the template. The gum or suction feature enables clean separation of template from the flat sheet. When the template is operable with gum, the template is affixed to the flat sheet and the combination moved to the coating apparatus where the sections of flat sheet are coated with one or more herbal essences to produce the section coated substrate and template combination (FIG. 17C). After removal from the coating apparatus, the template separated from the section coated substrate to produce section coated substrate 1700 of FIG. 17D. In a typical process, the template is disposable and inexpensive so that each single article coated substrate 1700 will be combined with a separate disposable template. In another embodiment involving a disposable template, the section coated substrate 1700 may be produced by a non-thermal process utilizing a composition of herbal essence or essences in volatile solvent. As shown in FIG. 17E, the liquid mixture of herbal essence and solvent 1752 is delivered through a controlled valve delivery mechanism to the combination of flat sheet 1702 and sectioned template 1704 as the combination moves along conveyer 1756. The delivery of mixture 1752 is coordinated with the movement of the combination so that mixture 1752 is applied to the sections 1706 of flat sheet 1702 outlined by the template rows 1710 (FIG. 17C). The combination is dried as it exits the conveyer 1756 to volatilize solvent form mixture 1752 and produce solid sections 1706 of herbal essence (FIG. 17C). The single article coated substrates 1700 with disposable templates 1704 may be stacked together for storage as shown at the right side of FIG. 17E.

When the template is operable with a suction feature for affixing to the flat sheet, the template may be a functionable part of a mechanical arm feature of the apparatus. The template may be constructed from permanent substantial material such as ceramic, metal or plastic capable of withstanding high temperatures. the template is further constructed with bores in the outline material of the template. The bores enable application of vacuum suction between the template and flat sheet to temporarily attach them together. The vacuum enables the template to appropriately and releasably attach by suction to the flat sheet. The arm would move to a flat sheet storage bin, place the template onto a flat sheet and apply vacuum suction to hold the template onto the flat plate. The arm with the suction template enables and transports the flat plate to the apparatus for coating. Coating may be accomplished by spray, brush or other manner for applying either a composition of an herbal essence in volatile solvent or a vapor of herbal essence to sections of the flat plate. Following the coating process, the mechanical arm with template and coated flat sheet transports the coated sheet to a holding bin, releases the coated sheet and returns to place the template on the next flat sheet for transport to the apparatus for coating. The template with vacuum bores enables an ease of attachment and detachment of the flat plate.

With the template arrangement as a permanent part of the coating apparatus or as a part to be affixed temporarily to the flat sheet, this process enables ready, efficient production of the substrate with separate sections of one or more herbal essences and minimizes and/or avoids the need for preparation of connectors and mesh mated with to the flat sheet as described above.

Figure 19A:
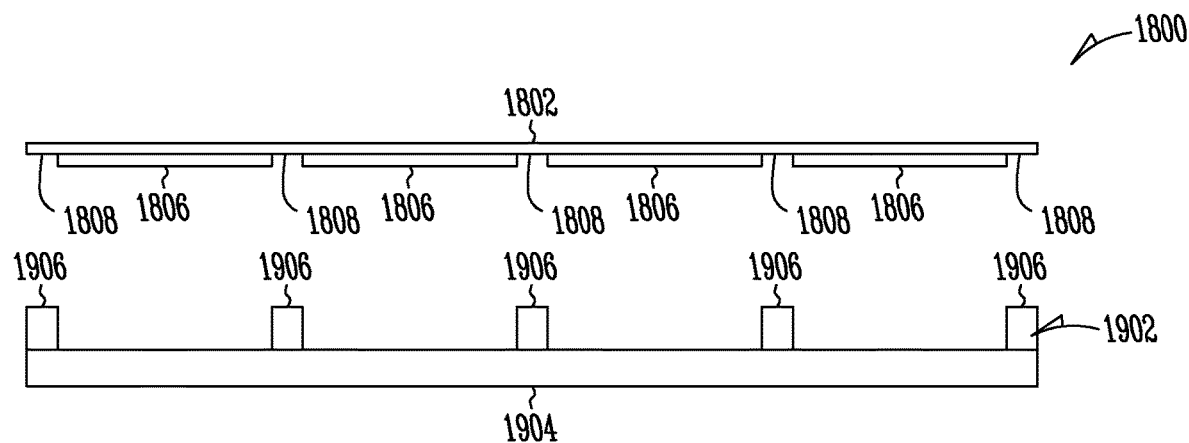
FIGS. 19A and 19B disclose a coated substrate with non-conductive holding frame.
Figure 19B:
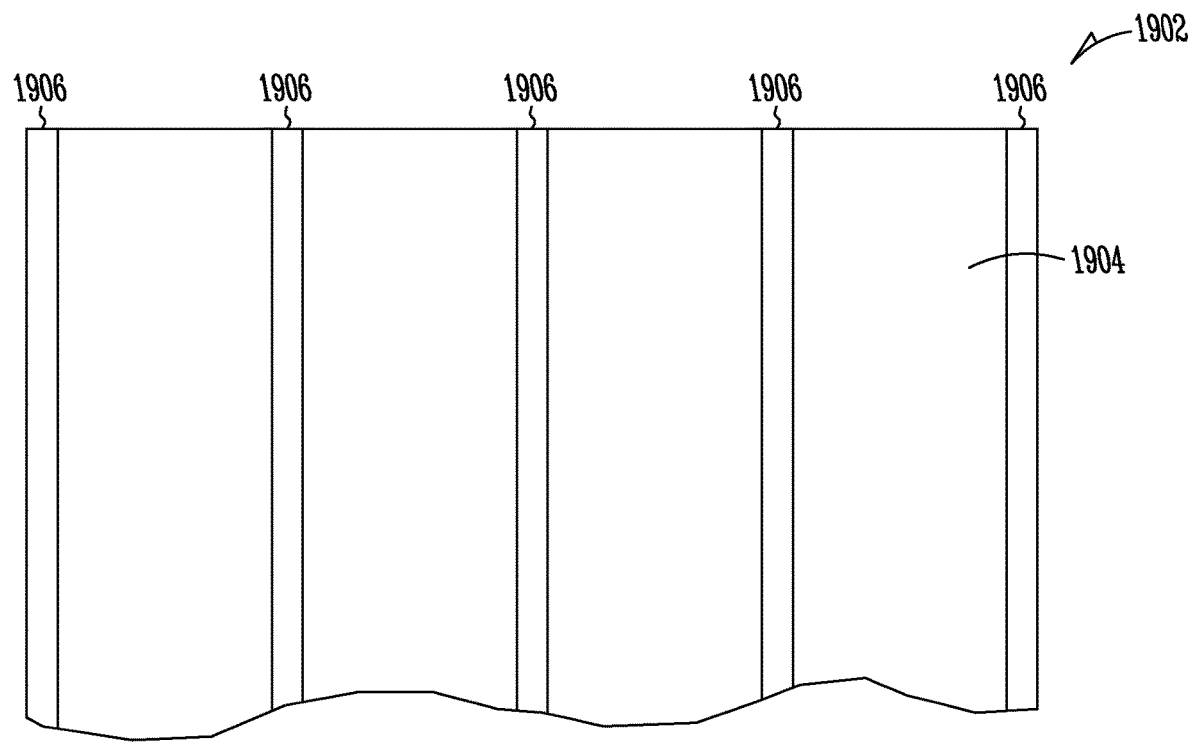

The single article coated substrate 1800 (same as 1700, FIG. 17D) with separate sections 1806 of one or more herbal essence coatings (FIG. 18B, FIG. 19A) may be combined with a non-conductive holding frame 1902 (FIG. 19A). The holding frame 1902 may be designed like the template outline 1704 described above for forming the separate sections of herbal essence. With this design, the holding frame 1902 has a border and bars 1906 which fit around the edges 1808 of the single article coated substrate and fit into the spaces 1808 between the separate sections 1806 of herbal essence coatings on substrate 1802. In one embodiment, the border and bars design of frame 1902 is open in the frame regions corresponding to section 1806 of the coated substrate so that the frame 1902 does not cover the separate sections 1806 of herbal essence coatings. In this embodiment, the frame 1902 may also function as the disposable template described above. In another embodiment, holding frame 1802 may also be designed as a continuous platform 1904 to which is attached bars or protrusions 1906. The single article coated substrate 1800 (FIG. 18B) may be fitted onto this holding frame 1902 so that the bars or protrusions 1906 fit into the spaces 1808 between the separate sections 1806 of herbal essence coating. In this embodiment, the platform 1904 of the holding frame 1902 covers the regions corresponding to the sections 1806 of the herbal essence coatings. Either holding frame design may be combined with the single article coated substrate 1800 prepared by any of the procedures described above including the permanent template attached to the coating apparatus and the temporary template attached to the flat sheet. As mentioned, with one embodiment of the temporary template process, the temporary template is disposable and also becomes the holding frame. In this embodiment, the holding frame has a border and bars and is open in frame regions corresponding to the sections 1806 of herbal essence coatings on substrate 1802 (FIG. 19A).

Figure 20:
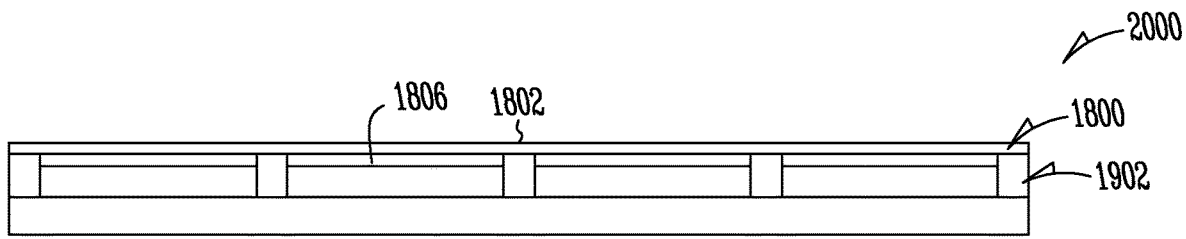
FIG. 20 discloses a combination of a coated substrate of FIG. 18B with holding frame.
Figure 21:
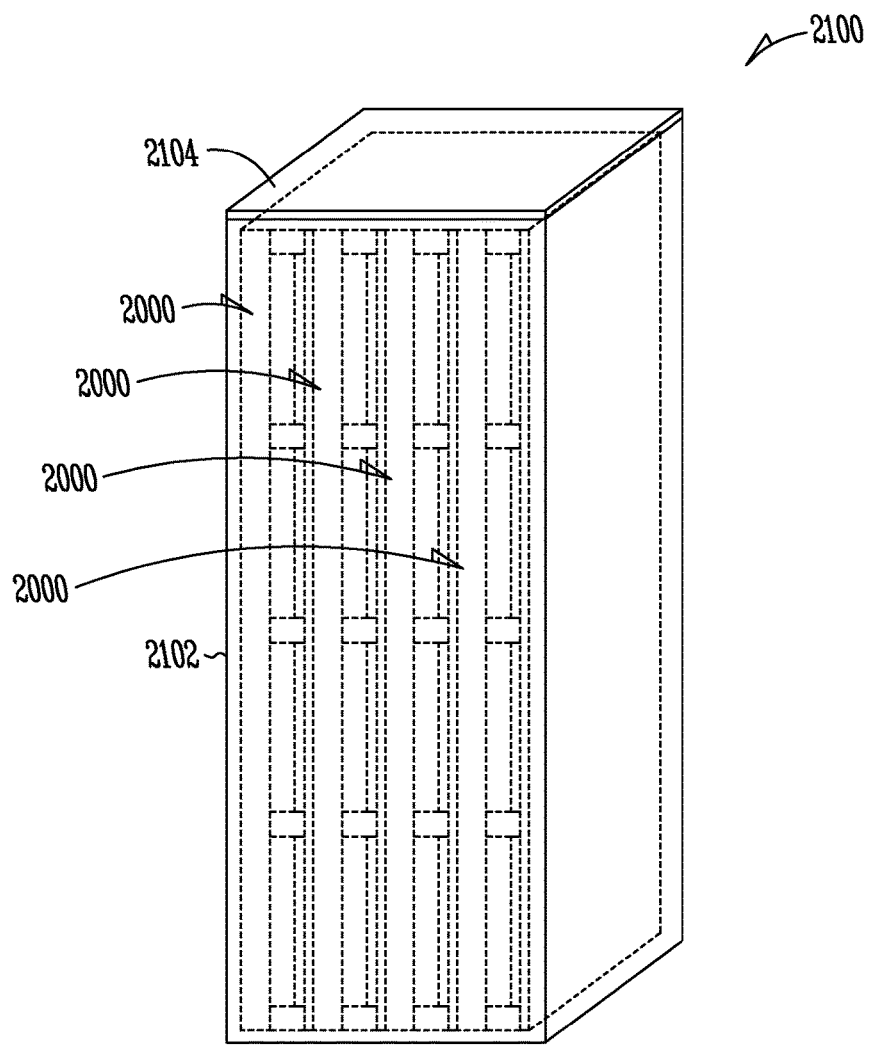
FIG. 21 discloses a package of the stack of FIG. 20.

With either design of the holding frame, open or covered, the combination of a post prep holding frame and single article coated substrate 1800 may also be formed following preparation of the single article coated substrate as described above using the permanent template/apparatus technique or the temporary template/arm technique. In this embodiment, the post prep holding frame is a post preparation material to be combined with the section coated substrate 1800 after the substrate sheet has been coated with herbal essence using a permanent or temporary template according to a thermal or solvent dissolution technique depicted by FIGS. 17A and 17E. An example of one version of the combination of single article coated substrate 1800 and post prep holding frame may be configured as depicted in FIG. 19A by consideration of 1902 as a post prep holding frame. The post prep holding frame 1902 may be constructed of a non-conductive material such as cardboard. The post prep holding frame has raised bars or protrusions 1906 that fit into the spaces 1808 between the separate sections 1806 of herbal essence coats of the coated substrate 1900. The combination of section coated substrate 1800 with post prep holding frame 1902 may be arranged into a group of framed, single article coated substrates for packaging into a container for use by a consumer. A package of single article coated substrates with post prep holding frames is depicted by FIGS. 20 and 21. FIG. 21 shows an example of a packaged product ready for shipment. The package shown by FIG. 21 is not a Vapor Cartridge directly insertable and operable in an herbal essence delivery device because the frames do not have bars of electrically conductor material.

Figure 22:
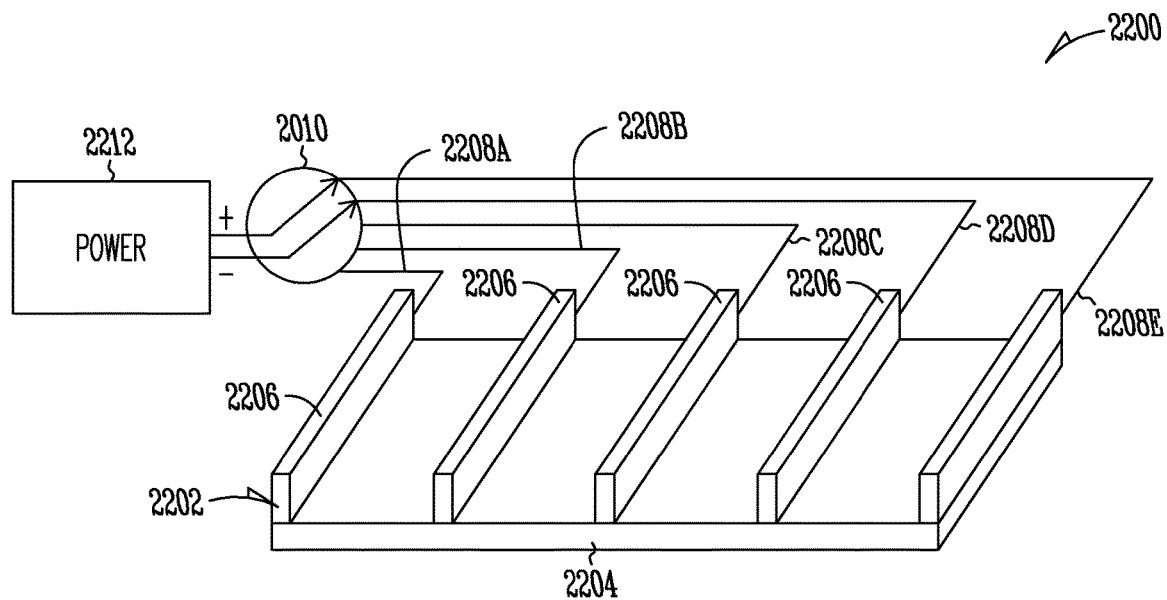
FIG. 22 discloses a grid with conductive rails.
Figure 23:
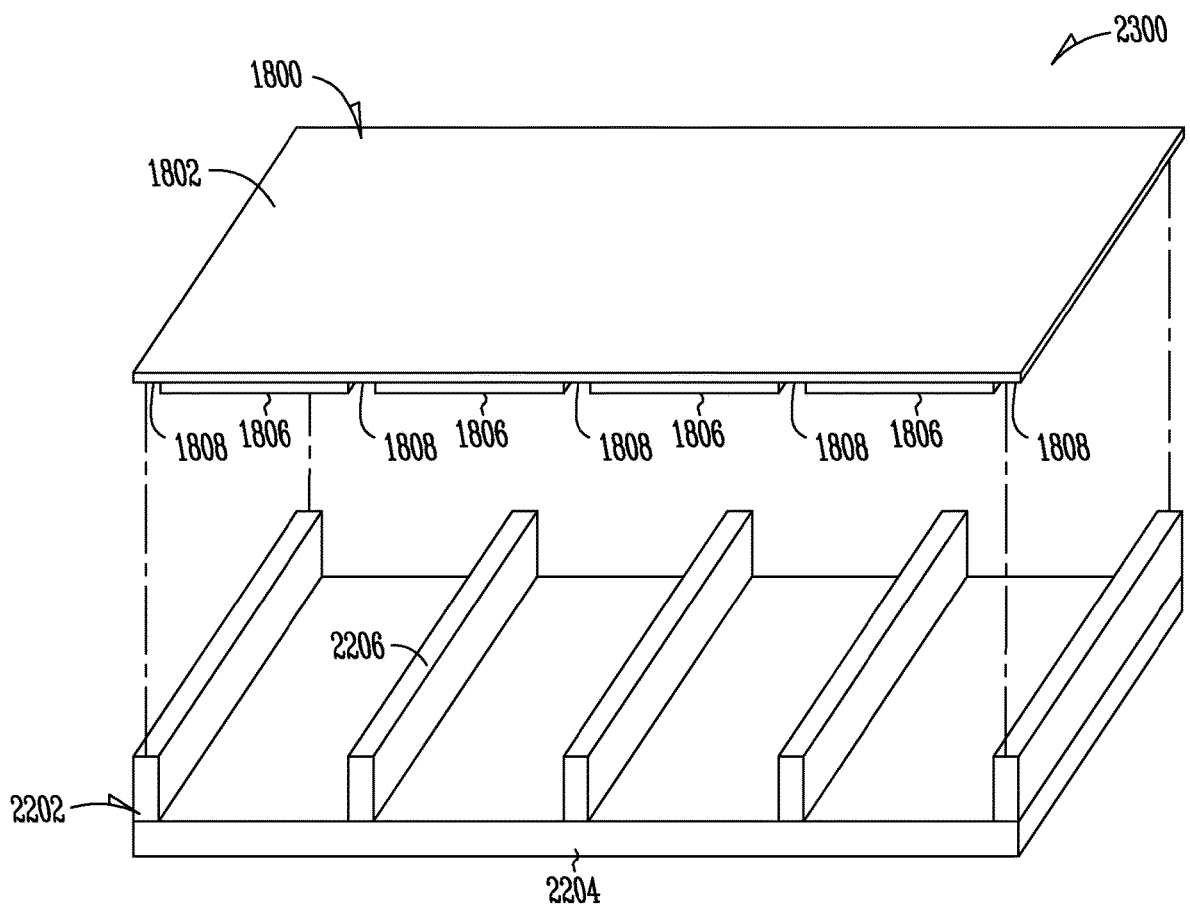
FIG. 23 discloses the combination of a coated substrate of FIG. 18B and grid with conductive rails of FIG. 22.
Figure 24:
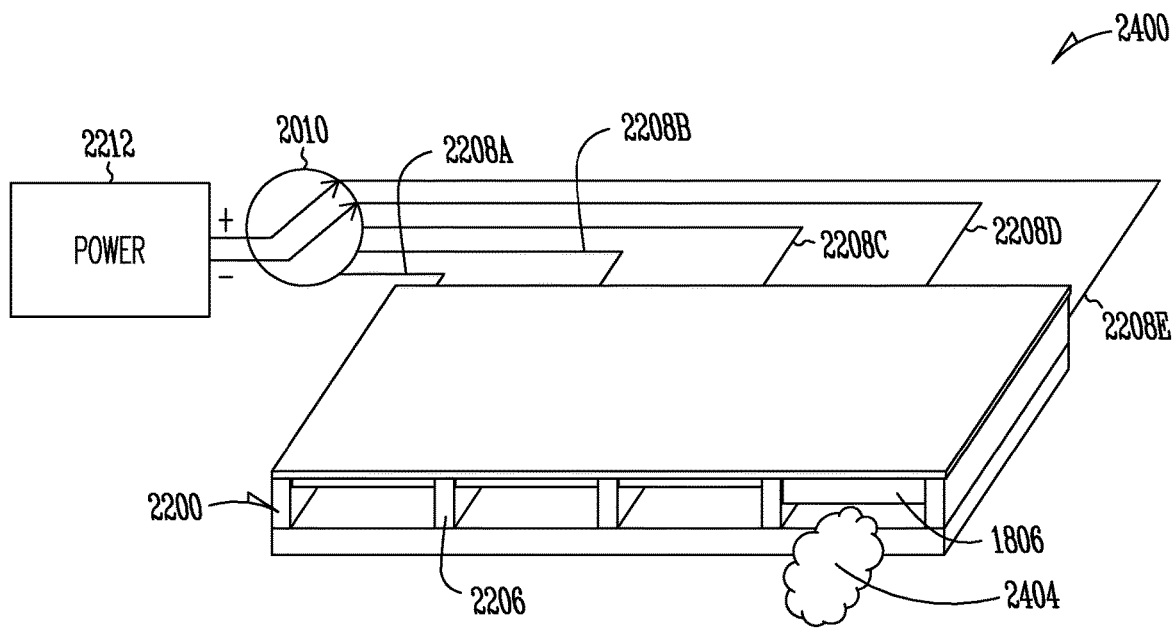
FIG. 24 discloses technique for powering the combination of FIG. 23.

An herbal essence delivery device can be configured as shown by FIGS. 22, 23, 24, 27 and 28 to receive the single article coated substrates. The delivery device depicted by FIG. 28 incorporates an activation grid 2200 (FIG. 22) which includes a conductor plate 2204 constructed with multiple power rails 2206 mounted on nonelectrically conductive bottom 2204 for applying current 2010 to the single article coated substrate 1800 (FIG. 23). Once the single article coated substrate 1800 is secured to the activation grid 2200, one or more sections of the substrate 1800 between rails 2206 can be electrified through the power rails 2206 of the activation grid 2200 driving an electrical current through corresponding sections of the conductive substrate 1800. The electrification of the power rail sections heats the one or more sections 1806 of herbal essence coating and causes the coating on that particular section or sections to volatilize into a vapor. FIG. 24 shows an example of activation chamber having four sections (2208A-B, 2208B-C, 2208C-D and 2208D-E) with section 2208D-E being electrified. The power rails 2206 of the activation grid 2200 fit into the spaces between the separate sections 1808 of herbal essence coatings on the single article coated substrate 1800 as shown by FIG. 24. As shown by FIG. 23, the electrically conductive channels 1808 of the coated substrate 1800 are the uncoated portions of the substrate 1802. These channels 1808 are in direct contact with the power rails 2206. Current may be applied to pairs of power rails such as is shown for rails 2208D and 2208E of FIGS. 22 and 24. The flat sheet is electrically conductive and generates resistive heating when a current is applied. Electric activation of rails 2208D and 2208E (FIG. 24) generates resistive heating only at the section 2402 of the single article coated substrate between the conductive channels of the coated substrate corresponding to rails 2208D and 2208E. The heating in turn volatilizes the corresponding section of herbal essence coating as shown by the mist 2404 of FIG. 24.

Figure 28:
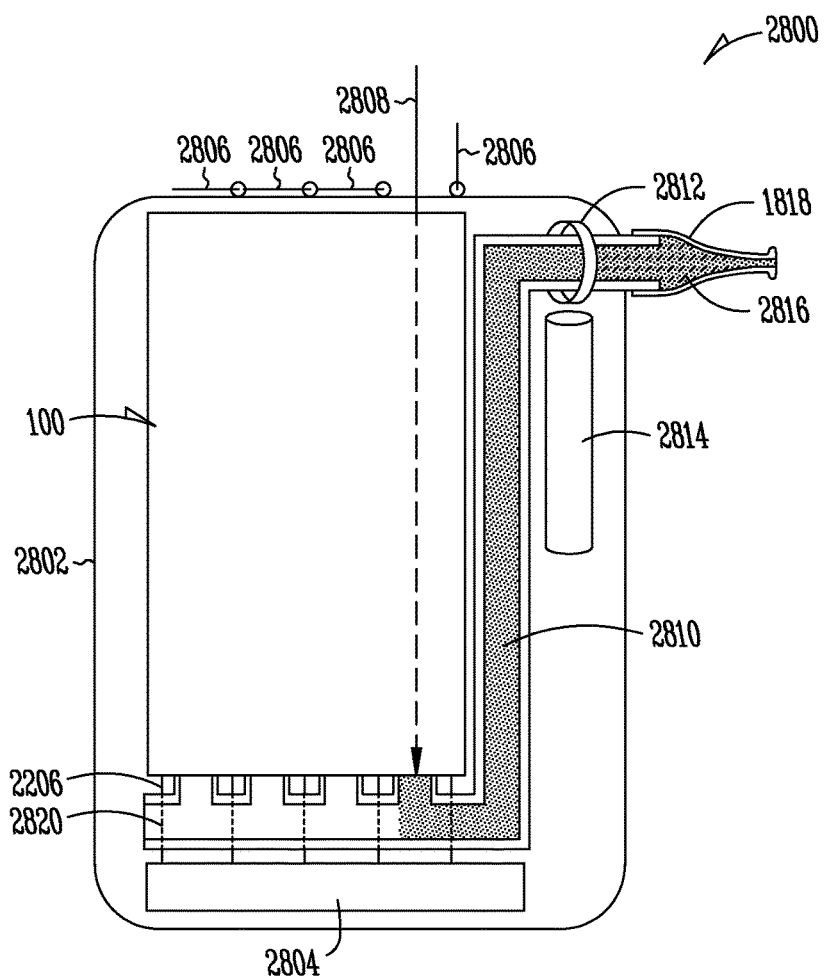
FIG. 28 discloses a device for use with a vapor cartridge.

The conductor plate with power rails, a.k.a. activation grid 2200 of FIG. 22 can be permanently mounted in an herbal essence delivery device shown by FIG. 28. The power rails 2206 are connected to the power and electronics bar 2804 by the wires 2820 shown in FIG. 28. The conductor plate 2204 of the activation grid 2200 is constructed of non-electrically conductive material so that only the rails mounted on the bottom conduct electricity. In this manner a circuit between two rails is formed only when the two rails are connected by the sheet 1802 of coated substrate 1800. The activation grid 2200 of FIG. 22 is permanently positioned underneath the "vapor cartridge" 100 of FIG. 28. The outer case 2802 of the device of FIG. 28 can be opened by a hinge at the bottom of the device. Upon opening the outer case, the single article coated substrate 1800 appearing as the vapor cartridge 100 of FIG. 28 can be removed and a new single article 1800 placed onto the power rails 2206. Closing the outer case and activating the power and electronics bar 2804 enables operation of the device. An air flow gate 2806 corresponding to the section of herbal essence coating to be volatilized (dotted line 2808) is opened either manually or electronically. Volatilized herbal essence is carried by the air flow in the direction indicated by the arrow 2808 and is carried through the air flow tube 2810 to the mouthpiece 1818 to be inhaled by the consumer.

Figure 25:
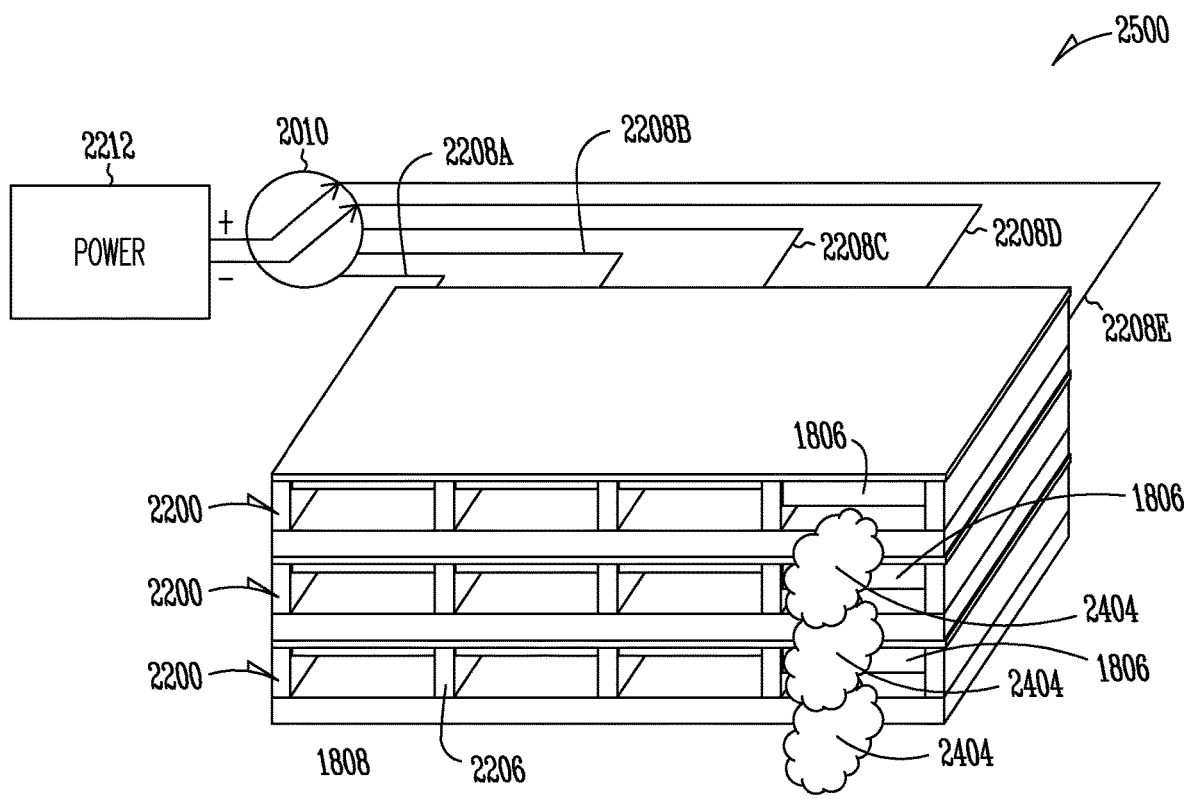
FIG. 25 discloses technique for powering a stack of the coated substrates of FIG. 18B according to the technique of FIG. 24.

In other embodiments of the single article coated substrate, the activation grid 2200 can be designed to receive multiple single article coated substrates 1800 as shown by FIG. 25. The activation chamber and case of the device 2800 (FIG. 28) may be arranged with one set of sides of the activation grid 2200 (FIG. 25) permanently attached to one side of the case housing 2802 (FIG. 28) and the other sides of the multiple activation grid are open and spaced so that the multiple activation grids form slots 2530 between them.

The plates 2204 of the activation grids 2200 are constructed of non-electrically conductive material so that only the rails mounted in the plates conduct electricity. In this manner a circuit between two rails is formed only when the two rails are connected by the coated substrate sheet 1800. The multiple single article coated substrates 1800 may be inserted into the slots 2530 so that the rails 2206 of each conductor plate 2200 (FIG. 25) fit onto the spaces 1808 between the sections 1806 of herbal essence coating substrates 1800. Closing the outer case enables the device with multiple single article coated substrates 1800 in the slots 2530 and mated with the rails 2206 of multiple activation grids 2200. The electric wire connections 2208A-E (FIG. 25) are made separately for each activation grid so that with three activation grids, there are fifteen A-E connections. Generally, with an appropriate multiple conductor plate arrangement in the housing case, the attachment between the activation grids 2200 and the housing is designed so that the single article coated substrates 1800 can be inserted onto the rails 2206 so as to sandwich the single articles coated substrates 1800 into the slots between the stacked multiple conductor plates. In one such embodiment, the sides of the activation grids 2200 to which the electrical connections A-E are made are also the sides permanently attached to the case housing 2802 (FIG. 28). In another embodiment, the two sides of the activation grids perpendicular to the side with the electrical connections A-E may be permanently attached to the case housing. When the case housing is open, the sides of the activation grids opposite the electrical connections are open so that the single article coated substrates 1800 may be fitted onto the rails of the activation grids by sliding the single article coated substrates into the slots between the activation grids.

Figure 26A:
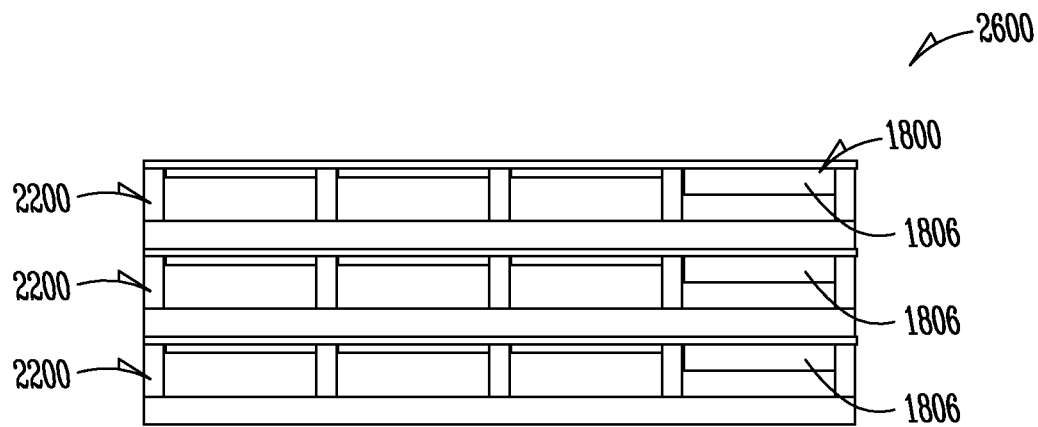
FIGS. 26A and 26B disclose air flow direction and section vaporization from a stack according to the technique of FIG. 25.

In an alternative design, the multiple activation grids 2200 can be permanently sandwiched together in a permanent frame for carrying multiple single article coated substrates 1800 as shown by FIG. 26A. The activation grids 2200 may be permanently bonded to a support frame 2630 attached to the sides of the grids 2200. The grids 2200 are spaced apart to provide the slots 2530 between individual grids 2200 for insertion of the single article substrates 1800 so that the substrates 1800 fit onto the rails 2206 of the grids. The plates 2204 of the grids 2200 are constructed of nonelectrically conductive material. The bottom 2204 of a grid 2200 and the rails 2206 of the adjacent grid 2200 form the slot into which the substrate 1800 fits so that the adjacent plate rails are mated with the spaces 1808 of coated substrate 1800. This arrangement enables plate 2204 to snuggly abut the bottom of sheet 1802 of the coated substrate 1800 so that the coated substrate 1810 mated tightly with the set of rails 2206 of the adjacent grid 2200. The backs of the grids 2200 are open to expose the ends of the grid rails. The multiple grids 2200, the bonded support frame 2630 and the inserted single article coated substrates 1800 constitute a vapor cartridge. The housing case of the delivery device may be opened and the cartridge placed into an appropriate niche of the delivery device. The niche of delivery device into which the vapor cartridge fits includes a set of electrical contacts arranged to mate with the ends of the conductor rails on the backs of the conductor plates. Activation and selective powering of the rails of the conductor plates operates as described above.

Figure 26B:
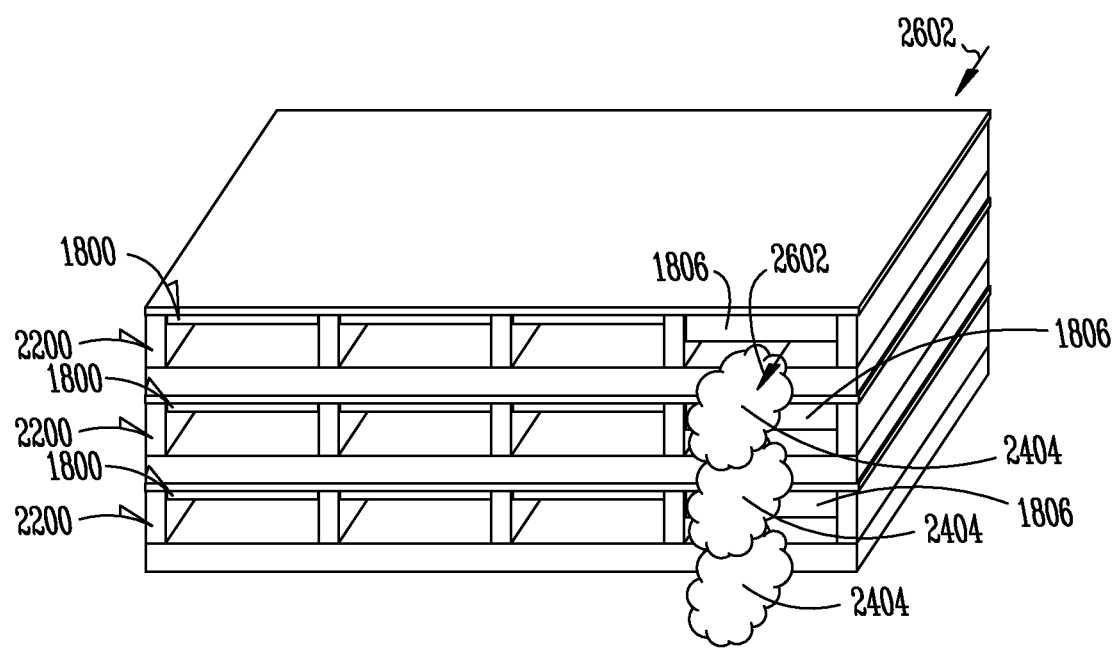
Figure 27:
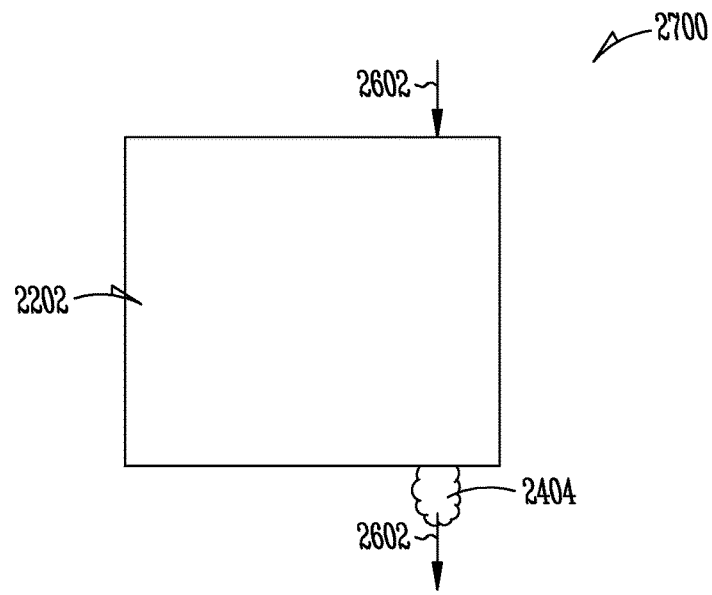
FIG. 27 discloses side view of stack with section vaporization depicted by FIGS. 26A and 26B.

After the herbal essences of the three single article coated substrates 1800 shown by FIGS. 25, 26 and 28 have been volatilized, the single articles can be removed from their slots in the delivery device or the vapor cartridge. If the embodiment includes a vapor cartridge, the individual single article substrates 1800 can be removed from the vapor cartridge frame just as they can be removed from their slots of the multiple conductor plates mounted in the delivery device housing. The spent single article substrates can be disposed and new single article coated substrates can then be inserted into the slots formed by the multiple grids 2200 mounted in the device housing or can be inserted into the slots formed by the multiple grids 2200 of the vapor cartridge frame. It may also be desirable to replace one of the three single article coated substrates 1800 which may be spent without replacing all three single article substrates 1800 some of which may not be spent. The design of the mounted multiple grids and/or the self-contained vapor cartridge make feasible single article replacement.

Extraction of Herbal Essences for Preparation of Coated Substrate

The herbal extract(s) can include any substance or agent having a pharmaceutical, physiological, medical, beneficial, sensory, perceived or unperceived but measurable effect upon a human. The substance or agent may be present in an herbaceous plant material or in a semi-synthetic derivative of plant material. In an example, the herbal extract component can include one or more active components for medicinal purposes, physiological action or therapeutic effect. In an example, the herbal extract component can include one or more extracts found in herbaceous plant material, including one or more of the plant materials such as herbal extracts of herbaceous plants. As discussed above, herbaceous plants in the context of the invention include spice and flavor producing plants, flowering plants, trees, bushes fungus, algae, medicinal agent plants, alkaloid producing plants, complex hydrocarbon producing plants and any kind of plant that has been found to contain or produce an organic compound that has a pharmacological, physiological, beneficial, naturopathic, sensory or other desired effect on a human. The herbal extracts may be polycyclic hydrocarbons, heterocycle compounds, saturated and unsaturated poly-hydrocarbon acids and esters, purines, pyrimidines, alkaloids, terpenes, steroidal compounds such as budesonide, mometasone or fluticasone, macrocycles, anti-infectives, naturally occurring esters, naturally occurring acids, naturally occurring amines, naturally occurring amides, naturally occurring Schiff bases and combinations and semi-synthetic derivatives thereof. These extracts may exhibit such therapeutic or physiologic effects as bronchodilator, cardiovascular, antibacterial, anti-infective, anti-viral, mucolytic, psychological, endocrine, gastrointestinal, digestive, anti-asthmatic, cardiopulmonary, renal, urogenital, reproductive, anti-conceptive, central nervous system, sympathetic and parasympathetic nervous system effects, skin, cranial-sinus, and other pharmacological effects. These therapeutic, pharmacological and/or physiologic effects are known attributes of the herbal extracts. Administration of herbal extracts that are controlled substances such as opiates and/or have significant pharmacological and/or physiological effects should be accomplished only under the guidance and wisdom of a registered M.D. or D.O. physician, nurse practitioner or physician's assistant who is qualified and licensed to prescribe such substances. In addition, purchase and use of such controlled substances made pursuant to aspects of this invention should only be made under the supervision and licensure of qualified pharmacists.

As an example, the herbaceous plants may be selected from the group consisting of damiana, blue lotus, mullein, lobelia, peppermint, spearmint, catnip, thyme, sage, wild dagga, lavender, rosemary, *Salvia divinorum*, basil, lemon balm, hops, yerba mate, *Calea zacatechichi*, chamomile, ashwagandha eucalyptus, passion flower, St John's wart, valerian, astragalus, *Avena sativa*, kinnikinnick, cacao, chago, cinnamon, nutmeg, mace, cordyceps, Don Quai, Gotu Kola, ginger root, ginseng, green tea, kava, maca, moringa leaf, mullein, sacred pink lotus, red raspberry, rhodiola, rooibos, tong kat ali, vanilla, yohimbine, garlic, turmeric, nutmeg, capsaicin, rosemary, *cannabis* aka marijuana, coniferous trees, yew bush, willow tree, aspen tree, blood root, opium poppy, *Atropa belladonna*, strychnine, *Vinca rosea*, coffee plant, cacao tree and beans (chocolate), coca plant (cocaine), nicotinaa *tabacum, Camelia sinensis*, monkshood, castor oil, henbane, calabar bean, *digitalis* sp, autumn crocus, peyote, amanita, orange, lemon, and similar known herbaceous plants in which useful herbal extracts are known to be present. Some of these herbal substances of extracts can be obtained commercially as they have previously been extracted for the herbaceous plant materials. Still others have been synthetically derivatized to form semi-synthetic compounds. The most useful forms of such herbal substances or extracts and semi-synthetic compounds are the free base or free acid forms or neutral, un-complexed forms. These forms lend themselves to volatilization and/or molecular entrainment as vapors and/or aerosols. The salt forms of bases and acids as well as complexed forms of neutral compounds can preferably be converted into the non-salt and/or non-complexed forms for use according to the invention.

The extracts of herbal plant material can exist in several parts of the plant including, but not limited to, leaves, stem, roots, branches, bark, flower, flower buds and/or fruit or seeds. In an example, the herbaceous plant material can include components such as all of the foregoing parts of a plant. As used herein, herbaceous plants can refer to plant material that has been harvested but is otherwise unprocessed. In an example, the plant material such as leaves, stems, bark, branches, seeds, roots, flowers and/or fruit can be shredded, chopped or otherwise comminuted to increase the surface area of the material in preparation for purification. In an example, the desired herbaceous material can include small particles produced by comminution. In an example, the herbal extract can be obtained by solvent extraction treatments or volatilization treatments or fractional distillation treatments of the comminuted herbaceous material.

Multiple literature references describe use of herbaceous plant material as a starting material for development of herbal essences. It is recognized that any herbaceous plant composition can be used in the processes for producing herbal essences. Some of the processing steps, such as the separation or purification step, may vary depending on whether herbaceous plant material or an alternative form of an herbal plant material composition is used. Any known process for production of herbal essences may be employed to produce the herbal essences and/or substances useful according to embodiments of the invention for formation of the one or more coatings of herbal essence on the substrate. While specific processing techniques for production of herbal essences are not a limitation of the invention, the thermal and extractive techniques set forth in the following discussion provide exemplary processes for such production.

In a process for production of herbal essence(s), a pre-processing step can include receiving source material, such as, for example, raw herbaceous plant material. In an example, the pre-processing step can include collection of raw herbaceous material from growers for use as source material and removal of undesirable organic and inorganic components from the source material. In an example, the source material can be a whole plant as discussed above or appropriate parts of the plant known to contain the desired herbal extract(s).

A first inspection step can include examination of the source material for general suitability in the process. In an example, source material that is diseased or not otherwise of a specified quality can be removed from the source material before further processing.

A source material preparation step can further prepare the source material for later steps in the process. In an example, the source material preparation step can include the use of equipment and methods to increase the surface area of the source material, such as by shredding, chopping or otherwise comminuting, to aid in a purification process.

A second inspection step can include examination of source material to ensure that the source material has been suitably processed. In an example, source material that has been improperly shredded or chopped may be rejected or redirected for further processing.

Purification and coating steps can be practiced using such techniques as heat volatilization or wet extraction for separating the herbal extracts from the herbaceous plants. These techniques are presented in U.S. Pat. Nos. 9,220,294 and 10,661,036, the disclosures of which are incorporated herein by reference. For heat volatilization, the purification can include heating the pre-processed plant material to volatilize the herbal extract(s). Specific steps can depend on the form of the herbaceous plant material. The volatilized herbal extract(s) can then be condensed directly onto a substrate such as a flat sheet to form a substrate coated with the herbal extract(s) or may be condensed and deposited in a storage container for subsequent coating on a substrate. In an example of direct condensation, the condensation of volatilized herbal extract(s) onto a substrate can be accomplished through cooled absorption or cooled adsorption of the volatilized herbal extract. In an example of storage condensation, the volatilized herbal extract(s) may be transported as vapors to a condenser apparatus which condenses the vapors to liquids, oils and/or solids and deposits the liquids, oils and/or solids in a storage container. The stored herbal essences may be re-volatilized by heat techniques at a later time to deposit the volatilized herbal extract on a substrate. Alternatively, herbal essences manufactured by third parties may be employed similarly to form herbal essence coatings on substrates by heat volatilization and cooled absorption or cooled adsorption o the volatized herbal extract(s) on the substrate(s). The purification and coating steps can also be practiced multiple times or simultaneously practiced with multiple apparatuses to produce multiple herbal extracts deposited as overlapping layers or segregated layers on the substrate.

Alternatively, the purification and coating step can include an extractive process for separating the herbal extract from the herbaceous plants. The appropriate plant material, e.g., the whole plant or selected plant parts such as flowers, seeds, buds, leaves, stems, branches, bark and/or roots, may be comminuted into very small particles. The small plant particles may be extracted with a solvent in which the desired herb extract is soluble to form an extract solution. In some examples, the solvent may be water while in others it may be ethyl alcohol, chloroform, supercritical carbon dioxide or a hydrocarbon. The extract solution may be decolorized with activated charcoal and/or further purified by column chromatography on diatomaceous earth or silica gel or other suitable known chromatographic support material, for example. The purified extract solution may be concentrated by substantial but not complete evaporation of the solvent to form a concentrate. The concentrate may be parsed onto the substrate and the remaining solvent evaporated to deposit the purified herbal extract on the substrate. Also, if the herbal extract is commercially available, it may be purchased in purified form and formulated in a minimum amount of appropriate solvent to form a concentrate as discussed above. The subsequent steps to form the purified herbal extract on the substrate may be carried out as described above. If multiple overlain layers of herbal extract are to be formed, subsequent layers may be deposited on top of previous layers by flash evaporation. As the subsequent concentrate is laid down over a previous layer, a flow of air or inert gas at a temperature to instantly evaporate the solvent is applied. The result is deposition of dry herbal extract and avoidance of comingling of the various layers that might result from solvent dissolution.

The volatilization process and the extraction process may be employed with a delivery system that will selectively deliver the one or more herbal substances to the substrate. The stream of herbal substance as a vapor from the heat volatilization process or as a composition of herbal substances in a volatile solvent may be transported to a device that can selectively deliver the vapor or composition to open sections of the substrate. Application may be made by spray nozzles, jet fingers or a film applicator. With the vapor, the transport and delivery features may be heated to preserve at least in part the vapor phase of the herbal substances.

MISCELLANEOUS STATEMENTS

The foregoing detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The foregoing description is intended to be illustrative, and not restrictive. For example, the above-described examples, statements and the embodiments (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A coated substrate comprising:
    a flat, electrically conductive sheet comprising two sides, side edges and front and back edges and comprising on one side a coating comprising one or more herbal essences, wherein the coating comprising one or more herbal essences is separated into sections with spaces free of herbal essences between the sections, each section having a length corresponding to the dimension of the sheet from the front to back edges and a width corresponding to a portion of the dimension of the sheet from one of the side edges to an opposing one of the side edges, the sum of the widths of the multiple sections and spaces being the dimension of the sheet from one of the side edges to an opposing one of the side edges; and
    multiple mesh structures positioned either on the side opposite the coating side or on the coating side, wherein each mesh structure has a length corresponding to the dimension of the sheet from the front to back edges and a width corresponding to the width of the coating sections so as to provide spaces between the mesh structures corresponding to the spaces between the section coatings.

2. A coated substrate according to claim 1 wherein the conductive sheet further comprises multiple conductors positioned on the side with coating or the side without coating.

3. A coated substrate according to claim 1 wherein multiple conductors are positioned either at the spaces on the coating side of the sheet or positioned on the side of the sheet opposite the coating and at locations corresponding to the spaces.

4. A coated substrate according to claim 3 wherein the conductors are positioned on the side of the sheet opposite the coating side.

5. A coated substrate according to claim 1 wherein the multiple mesh structures are positioned on the same side as the coating side and the mesh structures are coated by the one or more herbal essences.

6. A single article comprising the coated substrate according to claim 1.

7. A grid-substrate combination comprising the single article according to claim 6 in combination with a grid comprising a non-conductive plate with conductive rails wherein the rails of the grid mate with the spaces of the coated substrate, the plate of the grid having a length and width the same as the length and width of the flat electrically conductive sheet of the coated substrate.

8. A cartridge comprising stacked members of the grid-substrate combination of claim 7 wherein the stack has a length and width defined by the length and width of the grid-substrate combination and a height defined by the stack, and cartridge further comprises solid support structures attached to the sides of the grid plate defined by the edges of the plates and adjacent members of the stack define slots containing the single article such that the single articles are removable from the cartridge and are replacable by new single articles.

9. A coated substrate of claim 1 wherein the one or more herbal essences comprise at least one of CBD and THC.

10. A coated substrate of claim 1 wherein the one or more herbal essences comprise herbal extracts of one or more herbaceous plants.

11. A method for production of a coated substrate of claim 1 comprising combining a template and the conductive sheet so as to provide masked and unmasked areas of the sheet that will become the spaces between the sections of herbal essence coatings and become the sections of herbal essence coatings respectively and depositing one or more herbal essences onto the non-masked areas of the conductive sheet to provide the coated substrate.

12. A herbal essence delivery device suitable for production of herbal essence vapors comprising a housing with an air inlet, an air outlet, electronic controls and an internal niche for holding a cartridge comprising the coated substrate of claim 1, the housing configured to transport air from the air inlet through the cartridge and out through the air outlet, the outlet being configured at least in part as a mouthpiece.

13. A cartridge comprising:
a stack of multiple members of coated substrates, each coated substrate comprising
a flat, electrically conductive sheet comprising two sides, side edges and front and back edges and comprising on one side a coating comprising one or more herbal essences, and
multiple conductors positioned on the side with coating or the side without coating, wherein the multiple conductors are positioned either at the spaces on the coating side of the sheet or positioned on the side of the sheet opposite the coating side and at locations corresponding to the spaces;
wherein the conductors of the substrates are positioned on the sheet side opposite the coating and the conductors of one member fit into spaces between sections of the coating of an adjacent member of the stack.

14. A method for production of a cartridge of claim 13 comprising:
providing the electrically conductive sheet with multiple conductors;
depositing one or more herbal essences onto the sheet to form the coated substrate; and
stacking multiple coated substrates to form the cartridge.

15. A coated substrate with frame comprising:
a single article in combination with a non-conductive holding frame with bars, the single article comprising a coated substrate comprising
a flat, electrically conductive sheet comprising two sides, side edges and front and back edges and comprising on one side a coating comprising one or more herbal essences,
wherein the coating comprising one or more herbal essences is separated into sections with spaces free of herbal essences between the sections, each section having a length corresponding to the dimension of the sheet from the front to back edges and a width corresponding to a portion of the dimension of the sheet from one of the side edges to an opposing one of the side edges, the sum of the widths of the multiple sections and spaces being the dimension of the sheet from one of the side edges to an opposing one of the side edges;
wherein the bars of the frame mate with the spaces of the coated substrate thereby providing the coated substrate with frame.

16. A package of multiple numbers of the coated substrate with frame according to claim 15.

17. A method for production of the package according to claim 16 comprising:
providing an electrically conductive sheet;
depositing one or more herbal essences on to the conductive sheet as separate coating sections thereby producing the coated substrate;
combining the coated substrate and the non-conductive holding frame to form the coated substrate with frame; and
stacking a plurality of the coated sheets with frames to provide the package.

* * * * *